United States Patent
Nakai et al.

(10) Patent No.: US 10,064,583 B2
(45) Date of Patent: Sep. 4, 2018

(54) DETECTION OF EXPIRATORY AIRFLOW LIMITATION IN VENTILATED PATIENT

(71) Applicant: Covidien LP, Boulder, CO (US)

(72) Inventors: Richard Nakai, Long Beach, CA (US); Warren Sanborn, Escondido, CA (US); David Hyde, Oceanside, CA (US)

(73) Assignee: Covidien LP, Mansfield, MA (US)

( * ) Notice: Subject to any disclaimer, the term of this patent is extended or adjusted under 35 U.S.C. 154(b) by 1229 days.

(21) Appl. No.: 13/961,316

(22) Filed: Aug. 7, 2013

(65) Prior Publication Data

US 2015/0045687 A1 Feb. 12, 2015

(51) Int. Cl.
  *A61B 5/08* (2006.01)
  *A61B 5/00* (2006.01)
  *A61B 5/085* (2006.01)
  *A61M 16/00* (2006.01)
  *A61M 16/12* (2006.01)

(52) U.S. Cl.
  CPC ............ *A61B 5/7246* (2013.01); *A61B 5/085* (2013.01); *A61B 5/0816* (2013.01); *A61B 5/4836* (2013.01); *A61B 5/7282* (2013.01); *A61M 16/0051* (2013.01); *A61M 16/026* (2017.08); *A61M 16/12* (2013.01); *A61M 16/0063* (2014.02); *A61M 2016/0027* (2013.01); *A61M 2016/0036* (2013.01); *A61M 2016/0042* (2013.01); *A61M 2202/025* (2013.01); *A61M 2202/0208* (2013.01); *A61M 2205/505* (2013.01); *A61M 2205/52* (2013.01); *A61M 2230/46* (2013.01)

(58) Field of Classification Search
  None
  See application file for complete search history.

(56) References Cited

U.S. PATENT DOCUMENTS

| | | |
|---|---|---|
| 4,622,980 A | 11/1986 | Kunig |
| 4,739,987 A | 4/1988 | Nicholson |
| 4,752,089 A | 6/1988 | Carter |

(Continued)

OTHER PUBLICATIONS

7200 Series Ventilator, Options, and Accessories: Operator's Manual. Nellcor Puritan Bennett, Part No. 22300 A, Sep. 1990, pp. 1-196.

(Continued)

*Primary Examiner* — Tiffany Weston

(57) ABSTRACT

This disclosure describes systems and methods for monitoring and evaluating data associated with ventilatory parameters to detect expiratory airflow limitation in a ventilated patient. For example, a ventilator may monitor flow and/or pressure during ventilation of the patient. Based on the flow and/or pressure measurements, or ventilatory data derived therefrom, the ventilator may calculate expiratory resistance. Moreover, the ventilator may trend expiratory resistance over time to produce an expiratory resistance waveform. In embodiments, the ventilator may calculate the slope of the expiratory resistance waveform during an initial part of exhalation. If the slope of the expiratory resistance waveform during the initial part of exhalation breaches a defined slope threshold, the ventilator may determine that the patient exhibits expiratory airflow limitation.

20 Claims, 11 Drawing Sheets

(56) References Cited

U.S. PATENT DOCUMENTS

| | | |
|---|---|---|
| 4,921,642 A | 5/1990 | LaTorraca |
| 4,954,799 A | 9/1990 | Kumar |
| 5,057,822 A | 10/1991 | Hoffman |
| 5,072,737 A | 12/1991 | Goulding |
| 5,150,291 A | 9/1992 | Cummings et al. |
| 5,161,525 A | 11/1992 | Kimm et al. |
| 5,237,987 A | 8/1993 | Anderson et al. |
| 5,271,389 A | 12/1993 | Isaza et al. |
| 5,279,549 A | 1/1994 | Ranford |
| 5,299,568 A | 4/1994 | Forare et al. |
| 5,301,921 A | 4/1994 | Kumar |
| 5,319,540 A | 6/1994 | Isaza et al. |
| 5,325,861 A | 7/1994 | Goulding |
| 5,333,606 A | 8/1994 | Schneider et al. |
| 5,339,807 A | 8/1994 | Carter |
| 5,343,857 A | 9/1994 | Schneider et al. |
| 5,351,522 A | 10/1994 | Lura |
| 5,357,946 A | 10/1994 | Kee et al. |
| 5,368,019 A | 11/1994 | LaTorraca |
| 5,383,449 A | 1/1995 | Forare et al. |
| 5,385,142 A | 1/1995 | Brady et al. |
| 5,390,666 A | 2/1995 | Kimm et al. |
| 5,401,135 A | 3/1995 | Stoen et al. |
| 5,402,796 A | 4/1995 | Packer et al. |
| 5,407,174 A | 4/1995 | Kumar |
| 5,413,110 A | 5/1995 | Cummings et al. |
| 5,419,314 A | 5/1995 | Christopher |
| 5,438,980 A | 8/1995 | Phillips |
| 5,443,075 A | 8/1995 | Holscher |
| 5,513,631 A | 5/1996 | McWilliams |
| 5,517,983 A | 5/1996 | Deighan et al. |
| 5,520,071 A | 5/1996 | Jones |
| 5,524,615 A | 6/1996 | Power |
| 5,531,221 A | 7/1996 | Power |
| 5,542,415 A | 8/1996 | Brady |
| 5,544,674 A | 8/1996 | Kelly |
| 5,549,106 A | 8/1996 | Gruenke et al. |
| 5,582,182 A | 12/1996 | Hillsman |
| 5,596,984 A | 1/1997 | O'Mahony et al. |
| 5,630,411 A | 5/1997 | Holscher |
| 5,632,270 A | 5/1997 | O'Mahony et al. |
| 5,645,048 A | 7/1997 | Brodsky et al. |
| 5,660,171 A | 8/1997 | Kimm et al. |
| 5,664,560 A | 9/1997 | Merrick et al. |
| 5,664,562 A | 9/1997 | Bourdon |
| 5,671,767 A | 9/1997 | Kelly |
| 5,672,041 A | 9/1997 | Ringdahl et al. |
| 5,673,689 A | 10/1997 | Power |
| 5,715,812 A | 2/1998 | Deighan et al. |
| 5,762,480 A | 6/1998 | Adahan |
| 5,771,884 A | 6/1998 | Yarnell et al. |
| 5,791,339 A | 8/1998 | Winter |
| 5,794,986 A | 8/1998 | Gansel et al. |
| 5,813,399 A | 9/1998 | Isaza et al. |
| 5,826,575 A | 10/1998 | Lall |
| 5,829,441 A | 11/1998 | Kidd et al. |
| 5,864,938 A | 2/1999 | Gansel et al. |
| 5,865,168 A | 2/1999 | Isaza |
| 5,881,717 A | 3/1999 | Isaza |
| 5,881,723 A | 3/1999 | Wallace et al. |
| 5,884,623 A | 3/1999 | Winter |
| 5,909,731 A | 6/1999 | O'Mahony et al. |
| 5,915,379 A | 6/1999 | Wallace et al. |
| 5,915,380 A | 6/1999 | Wallace et al. |
| 5,915,382 A | 6/1999 | Power |
| 5,918,597 A | 7/1999 | Jones et al. |
| 5,921,238 A | 7/1999 | Bourdon |
| 5,934,274 A | 8/1999 | Merrick et al. |
| 5,944,680 A * | 8/1999 | Christopherson ........ A61B 5/03 128/897 |
| 6,024,089 A | 2/2000 | Wallace et al. |
| 6,041,780 A | 3/2000 | Richard et al. |
| 6,047,860 A | 4/2000 | Sanders |
| 6,076,523 A | 6/2000 | Jones et al. |
| 6,116,240 A | 9/2000 | Merrick et al. |
| 6,116,464 A | 9/2000 | Sanders |
| 6,123,073 A | 9/2000 | Schlawin et al. |
| 6,135,106 A | 10/2000 | Dirks et al. |
| 6,142,150 A | 11/2000 | O'Mahoney et al. |
| 6,161,539 A | 12/2000 | Winter |
| 6,220,245 B1 | 4/2001 | Takabayashi et al. |
| 6,269,812 B1 | 8/2001 | Wallace et al. |
| 6,273,444 B1 | 8/2001 | Power |
| 6,283,119 B1 | 9/2001 | Bourdon |
| 6,305,373 B1 | 10/2001 | Wallace et al. |
| 6,321,748 B1 | 11/2001 | O'Mahoney |
| 6,325,785 B1 | 12/2001 | Babkes et al. |
| 6,357,438 B1 | 3/2002 | Hansen |
| 6,360,745 B1 | 3/2002 | Wallace et al. |
| 6,369,838 B1 | 4/2002 | Wallace et al. |
| 6,412,483 B1 | 7/2002 | Jones et al. |
| 6,439,229 B1 | 8/2002 | Du et al. |
| 6,467,478 B1 | 10/2002 | Merrick et al. |
| 6,546,930 B1 | 4/2003 | Emerson et al. |
| 6,553,991 B1 | 4/2003 | Isaza |
| 6,557,553 B1 | 5/2003 | Borrello |
| 6,571,795 B2 | 6/2003 | Bourdon |
| 6,622,726 B1 | 9/2003 | Du |
| 6,644,310 B1 | 11/2003 | Delache et al. |
| 6,668,824 B1 | 12/2003 | Isaza et al. |
| 6,675,801 B2 | 1/2004 | Wallace et al. |
| 6,718,974 B1 | 4/2004 | Moberg |
| 6,725,447 B1 | 4/2004 | Gilman et al. |
| 6,739,337 B2 | 5/2004 | Isaza |
| 6,761,167 B1 | 7/2004 | Nadjafizadeh et al. |
| 6,761,168 B1 | 7/2004 | Nadjafizadeh et al. |
| 6,814,074 B1 | 11/2004 | Nadjafizadeh et al. |
| 6,866,040 B1 | 3/2005 | Bourdon |
| 6,960,854 B2 | 11/2005 | Nadjafizadeh et al. |
| 7,036,504 B2 | 5/2006 | Wallace et al. |
| 7,077,131 B2 | 7/2006 | Hansen |
| RE39,225 E | 8/2006 | Isaza et al. |
| 7,117,438 B2 | 10/2006 | Wallace et al. |
| 7,270,126 B2 | 9/2007 | Wallace et al. |
| 7,334,581 B2 | 2/2008 | Doshi |
| 7,369,757 B2 | 5/2008 | Farbarik |
| 7,370,650 B2 | 5/2008 | Nadjafizadeh et al. |
| 7,428,902 B2 | 9/2008 | Du et al. |
| 7,460,959 B2 | 12/2008 | Jafari |
| 7,487,773 B2 | 2/2009 | Li |
| 7,654,802 B2 | 2/2010 | Crawford, Jr. et al. |
| 7,676,276 B2 | 3/2010 | Karell |
| 7,694,677 B2 | 4/2010 | Tang |
| 7,717,113 B2 | 5/2010 | Andrieux |
| D618,356 S | 6/2010 | Ross |
| 7,735,491 B2 | 6/2010 | Doshi et al. |
| 7,735,492 B2 | 6/2010 | Doshi et al. |
| 7,784,461 B2 | 8/2010 | Figueiredo et al. |
| 7,798,148 B2 | 9/2010 | Doshi et al. |
| 7,823,588 B2 | 11/2010 | Hansen |
| 7,855,716 B2 | 12/2010 | McCreary et al. |
| D632,796 S | 2/2011 | Ross et al. |
| D632,797 S | 2/2011 | Ross et al. |
| 7,891,354 B2 | 2/2011 | Farbarik |
| 7,893,560 B2 | 2/2011 | Carter |
| D638,852 S | 5/2011 | Skidmore et al. |
| 7,984,714 B2 | 7/2011 | Hausmann et al. |
| D643,535 S | 8/2011 | Ross et al. |
| 7,992,557 B2 | 8/2011 | Nadjafizadeh et al. |
| 7,992,563 B2 | 8/2011 | Doshi |
| 7,992,564 B2 | 8/2011 | Doshi et al. |
| 8,001,967 B2 | 8/2011 | Wallace et al. |
| D645,158 S | 9/2011 | Sanchez et al. |
| 8,020,700 B2 | 9/2011 | Doshi et al. |
| 8,021,310 B2 | 9/2011 | Sanborn et al. |
| D649,157 S | 11/2011 | Skidmore et al. |
| D652,521 S | 1/2012 | Ross et al. |
| D652,936 S | 1/2012 | Ross et al. |
| D653,749 S | 2/2012 | Winter et al. |
| 8,113,062 B2 | 2/2012 | Graboi et al. |
| D655,405 S | 3/2012 | Winter et al. |
| D655,809 S | 3/2012 | Winter et al. |
| D656,237 S | 3/2012 | Sanchez et al. |
| 8,172,765 B2 | 5/2012 | Maksym et al. |

(56) References Cited

U.S. PATENT DOCUMENTS

| | | |
|---|---|---|
| 8,181,645 B2 | 5/2012 | Houzego et al. |
| 8,181,648 B2 | 5/2012 | Perine et al. |
| 8,181,656 B2 | 5/2012 | Danek et al. |
| 8,210,173 B2 | 7/2012 | Vandine |
| 8,210,174 B2 | 7/2012 | Farbarik |
| 8,215,308 B2 | 7/2012 | Doshi et al. |
| 8,235,046 B2 | 8/2012 | Doshi et al. |
| 8,240,309 B2 | 8/2012 | Doshi et al. |
| 8,240,684 B2 | 8/2012 | Ross et al. |
| 8,267,085 B2 | 9/2012 | Jafari et al. |
| 8,272,379 B2 | 9/2012 | Jafari et al. |
| 8,272,380 B2 | 9/2012 | Jafari et al. |
| 8,291,909 B2 | 10/2012 | Doshi et al. |
| 8,302,600 B2 | 11/2012 | Andrieux et al. |
| 8,302,602 B2 | 11/2012 | Andrieux et al. |
| 8,302,606 B2 | 11/2012 | Doshi et al. |
| 8,312,879 B2 | 11/2012 | Choncholas et al. |
| 8,347,883 B2 | 1/2013 | Bird |
| 8,365,736 B2 | 2/2013 | Doshi et al. |
| 8,457,706 B2 | 6/2013 | Baker, Jr. |
| D692,556 S | 10/2013 | Winter |
| D693,001 S | 11/2013 | Winter |
| D701,601 S | 3/2014 | Winter |
| 8,792,949 B2 | 7/2014 | Baker, Jr. |
| D731,048 S | 6/2015 | Winter |
| D731,049 S | 6/2015 | Winter |
| D731,065 S | 6/2015 | Winter |
| D736,905 S | 8/2015 | Winter |
| D744,095 S | 11/2015 | Winter |
| 2001/0052344 A1 | 12/2001 | Doshi |
| 2003/0100843 A1 | 5/2003 | Hoffman |
| 2003/0159693 A1 | 8/2003 | Melker et al. |
| 2004/0194780 A1 | 10/2004 | Doshi |
| 2005/0039748 A1 | 2/2005 | Andrieux |
| 2005/0076907 A1 | 4/2005 | Stenzler |
| 2005/0139212 A1 | 6/2005 | Bourdon |
| 2005/0161046 A1 | 7/2005 | Michaels |
| 2005/0178385 A1* | 8/2005 | Dellaca' ............... A61B 5/085 128/204.23 |
| 2006/0032497 A1 | 2/2006 | Doshi |
| 2007/0017515 A1 | 1/2007 | Wallace et al. |
| 2007/0077200 A1 | 4/2007 | Baker |
| 2007/0185406 A1 | 8/2007 | Goldman |
| 2007/0227537 A1 | 10/2007 | Bemister et al. |
| 2007/0272241 A1 | 11/2007 | Sanborn et al. |
| 2007/0284361 A1 | 12/2007 | Nadjafizadeh et al. |
| 2008/0053441 A1 | 3/2008 | Gottlib et al. |
| 2008/0072896 A1 | 3/2008 | Setzer et al. |
| 2008/0072902 A1 | 3/2008 | Setzer et al. |
| 2008/0078390 A1 | 4/2008 | Milne et al. |
| 2008/0083644 A1 | 4/2008 | Janbakhsh et al. |
| 2008/0092894 A1 | 4/2008 | Nicolazzi et al. |
| 2008/0097234 A1 | 4/2008 | Nicolazzi et al. |
| 2008/0149097 A1 | 6/2008 | Haj-Yehia |
| 2008/0202517 A1 | 8/2008 | Mitton et al. |
| 2008/0221470 A1 | 9/2008 | Sather et al. |
| 2009/0025713 A1 | 1/2009 | Keller et al. |
| 2009/0145441 A1 | 6/2009 | Doshi et al. |
| 2009/0156978 A1 | 6/2009 | Faul et al. |
| 2009/0165795 A1 | 7/2009 | Nadjafizadeh et al. |
| 2009/0171176 A1 | 7/2009 | Andersohn |
| 2009/0194109 A1 | 8/2009 | Doshi et al. |
| 2009/0205661 A1 | 8/2009 | Stephenson et al. |
| 2009/0205663 A1 | 8/2009 | Vandine et al. |
| 2009/0241952 A1 | 10/2009 | Nicolazzi et al. |
| 2009/0241953 A1 | 10/2009 | Vandine et al. |
| 2009/0241956 A1 | 10/2009 | Baker, Jr. et al. |
| 2009/0241957 A1 | 10/2009 | Baker, Jr. |
| 2009/0241958 A1 | 10/2009 | Baker, Jr. |
| 2009/0241962 A1 | 10/2009 | Jafari et al. |
| 2009/0247849 A1 | 10/2009 | McCutcheon et al. |
| 2009/0247853 A1 | 10/2009 | Debreczeny |
| 2009/0247891 A1 | 10/2009 | Wood |
| 2009/0301486 A1 | 12/2009 | Masic |
| 2009/0301487 A1 | 12/2009 | Masic |
| 2009/0301490 A1 | 12/2009 | Masic |
| 2009/0301491 A1 | 12/2009 | Masic et al. |
| 2009/0314291 A1 | 12/2009 | Anderson et al. |
| 2010/0000528 A1 | 1/2010 | Palmer et al. |
| 2010/0011307 A1 | 1/2010 | Desfossez et al. |
| 2010/0024820 A1 | 2/2010 | Bourdon |
| 2010/0051026 A1 | 3/2010 | Graboi |
| 2010/0051029 A1 | 3/2010 | Jafari et al. |
| 2010/0069761 A1 | 3/2010 | Karst et al. |
| 2010/0071689 A1 | 3/2010 | Thiessen |
| 2010/0071692 A1 | 3/2010 | Porges |
| 2010/0071695 A1 | 3/2010 | Thiessen |
| 2010/0071696 A1 | 3/2010 | Jafari |
| 2010/0071697 A1 | 3/2010 | Jafari et al. |
| 2010/0078017 A1 | 4/2010 | Andrieux et al. |
| 2010/0078026 A1 | 4/2010 | Andrieux et al. |
| 2010/0081119 A1 | 4/2010 | Jafari et al. |
| 2010/0081955 A1 | 4/2010 | Wood, Jr. et al. |
| 2010/0139660 A1 | 6/2010 | Adahan |
| 2010/0147303 A1 | 6/2010 | Jafari et al. |
| 2010/0186744 A1 | 7/2010 | Andrieux |
| 2010/0218765 A1 | 9/2010 | Jafari et al. |
| 2010/0218766 A1 | 9/2010 | Milne |
| 2010/0218767 A1 | 9/2010 | Jafari et al. |
| 2010/0236555 A1 | 9/2010 | Jafari et al. |
| 2010/0242961 A1 | 9/2010 | Mougel et al. |
| 2010/0249549 A1 | 9/2010 | Baker, Jr. et al. |
| 2010/0282259 A1 | 11/2010 | Figueiredo et al. |
| 2010/0286548 A1 | 11/2010 | Lazar et al. |
| 2010/0288283 A1 | 11/2010 | Campbell et al. |
| 2010/0300442 A1 | 12/2010 | Houzego et al. |
| 2010/0300446 A1 | 12/2010 | Nicolazzi et al. |
| 2011/0005520 A1 | 1/2011 | Doshi et al. |
| 2011/0011400 A1 | 1/2011 | Gentner et al. |
| 2011/0023878 A1 | 2/2011 | Thiessen |
| 2011/0023879 A1 | 2/2011 | Vandine et al. |
| 2011/0023880 A1 | 2/2011 | Thiessen |
| 2011/0023881 A1 | 2/2011 | Thiessen |
| 2011/0029910 A1 | 2/2011 | Thiessen |
| 2011/0041849 A1 | 2/2011 | Chen et al. |
| 2011/0041850 A1 | 2/2011 | Vandine et al. |
| 2011/0108041 A1 | 5/2011 | Sather et al. |
| 2011/0126829 A1 | 6/2011 | Carter et al. |
| 2011/0126832 A1 | 6/2011 | Winter et al. |
| 2011/0126834 A1 | 6/2011 | Winter et al. |
| 2011/0126835 A1 | 6/2011 | Winter et al. |
| 2011/0126836 A1 | 6/2011 | Winter et al. |
| 2011/0126837 A1 | 6/2011 | Winter et al. |
| 2011/0128008 A1 | 6/2011 | Carter |
| 2011/0132361 A1 | 6/2011 | Sanchez |
| 2011/0132362 A1 | 6/2011 | Sanchez |
| 2011/0132364 A1 | 6/2011 | Ogilvie et al. |
| 2011/0132365 A1 | 6/2011 | Patel et al. |
| 2011/0132366 A1 | 6/2011 | Ogilvie et al. |
| 2011/0132367 A1 | 6/2011 | Patel |
| 2011/0132368 A1 | 6/2011 | Sanchez et al. |
| 2011/0132369 A1 | 6/2011 | Sanchez |
| 2011/0132371 A1 | 6/2011 | Sanchez et al. |
| 2011/0133936 A1 | 6/2011 | Sanchez et al. |
| 2011/0138308 A1 | 6/2011 | Palmer et al. |
| 2011/0138309 A1 | 6/2011 | Skidmore et al. |
| 2011/0138311 A1 | 6/2011 | Palmer |
| 2011/0138315 A1 | 6/2011 | Vandine et al. |
| 2011/0138323 A1 | 6/2011 | Skidmore et al. |
| 2011/0146681 A1 | 6/2011 | Jafari et al. |
| 2011/0146683 A1 | 6/2011 | Jafari et al. |
| 2011/0154241 A1 | 6/2011 | Skidmore et al. |
| 2011/0175728 A1 | 7/2011 | Baker, Jr. |
| 2011/0196251 A1 | 8/2011 | Jourdain et al. |
| 2011/0209702 A1 | 9/2011 | Vuong et al. |
| 2011/0209704 A1 | 9/2011 | Jafari et al. |
| 2011/0209707 A1 | 9/2011 | Terhark |
| 2011/0213215 A1 | 9/2011 | Doyle et al. |
| 2011/0218451 A1 | 9/2011 | Lai et al. |
| 2011/0230780 A1 | 9/2011 | Sanborn et al. |
| 2011/0249006 A1 | 10/2011 | Wallace et al. |
| 2011/0259330 A1 | 10/2011 | Jafari et al. |
| 2011/0259332 A1 | 10/2011 | Sanchez et al. |
| 2011/0259333 A1 | 10/2011 | Sanchez et al. |

(56) References Cited

U.S. PATENT DOCUMENTS

| | | |
|---|---|---|
| 2011/0265024 A1 | 10/2011 | Leone et al. |
| 2011/0271960 A1 | 11/2011 | Milne et al. |
| 2011/0273299 A1 | 11/2011 | Milne et al. |
| 2012/0000467 A1 | 1/2012 | Milne et al. |
| 2012/0000468 A1 | 1/2012 | Milne et al. |
| 2012/0000469 A1 | 1/2012 | Milne et al. |
| 2012/0000470 A1 | 1/2012 | Milne et al. |
| 2012/0029317 A1 | 2/2012 | Doyle et al. |
| 2012/0030611 A1 | 2/2012 | Skidmore |
| 2012/0060841 A1 | 3/2012 | Crawford, Jr. et al. |
| 2012/0071729 A1 | 3/2012 | Doyle et al. |
| 2012/0090611 A1 | 4/2012 | Graboi et al. |
| 2012/0096381 A1 | 4/2012 | Milne et al. |
| 2012/0103337 A1 | 5/2012 | Avni |
| 2012/0133519 A1 | 5/2012 | Milne et al. |
| 2012/0136222 A1 | 5/2012 | Doyle et al. |
| 2012/0137249 A1 | 5/2012 | Milne et al. |
| 2012/0137250 A1 | 5/2012 | Milne et al. |
| 2012/0167885 A1 | 7/2012 | Masic et al. |
| 2012/0185792 A1 | 7/2012 | Kimm et al. |
| 2012/0197578 A1 | 8/2012 | Vig et al. |
| 2012/0197580 A1 | 8/2012 | Vij et al. |
| 2012/0211008 A1 | 8/2012 | Perine et al. |
| 2012/0216809 A1 | 8/2012 | Milne et al. |
| 2012/0216810 A1 | 8/2012 | Jafari et al. |
| 2012/0216811 A1 | 8/2012 | Kimm et al. |
| 2012/0226444 A1 | 9/2012 | Milne et al. |
| 2012/0247471 A1 | 10/2012 | Masic et al. |
| 2012/0272960 A1 | 11/2012 | Milne |
| 2012/0272961 A1 | 11/2012 | Masic et al. |
| 2012/0272962 A1 | 11/2012 | Doyle et al. |
| 2012/0277616 A1 | 11/2012 | Sanborn et al. |
| 2012/0279501 A1 | 11/2012 | Wallace et al. |
| 2012/0285470 A9 | 11/2012 | Sather et al. |
| 2012/0289852 A1* | 11/2012 | Van Den Aardweg ............ A61B 5/085 600/533 |
| 2012/0304995 A1 | 12/2012 | Kauc |
| 2012/0304997 A1 | 12/2012 | Jafari et al. |
| 2013/0000644 A1 | 1/2013 | Thiessen |
| 2013/0006133 A1 | 1/2013 | Doyle et al. |
| 2013/0006134 A1 | 1/2013 | Doyle et al. |
| 2013/0008443 A1 | 1/2013 | Thiessen |
| 2013/0025596 A1 | 1/2013 | Jafari et al. |
| 2013/0025597 A1 | 1/2013 | Doyle et al. |
| 2013/0032151 A1 | 2/2013 | Adahan |
| 2013/0042869 A1 | 2/2013 | Andrieux et al. |
| 2013/0047983 A1 | 2/2013 | Andrieux et al. |
| 2013/0047989 A1 | 2/2013 | Vandine et al. |
| 2013/0053717 A1 | 2/2013 | Vandine et al. |
| 2013/0074844 A1 | 3/2013 | Kimm et al. |
| 2013/0081536 A1 | 4/2013 | Crawford, Jr. et al. |
| 2013/0104896 A1 | 5/2013 | Kimm et al. |
| 2013/0146055 A1 | 6/2013 | Jafari et al. |
| 2013/0152923 A1 | 6/2013 | Andrieux et al. |
| 2013/0158370 A1 | 6/2013 | Doyle et al. |
| 2013/0159912 A1 | 6/2013 | Baker, Jr. |
| 2013/0167842 A1 | 7/2013 | Jafari et al. |
| 2013/0167843 A1 | 7/2013 | Kimm et al. |
| 2013/0186397 A1 | 7/2013 | Patel |
| 2013/0186400 A1 | 7/2013 | Jafari et al. |
| 2013/0186401 A1 | 7/2013 | Jafari et al. |
| 2013/0192599 A1 | 8/2013 | Nakai et al. |
| 2013/0220324 A1 | 8/2013 | Jafari et al. |
| 2013/0233314 A1 | 9/2013 | Jafari et al. |
| 2013/0233319 A1 | 9/2013 | Winter et al. |
| 2013/0239038 A1 | 9/2013 | Skidmore et al. |
| 2013/0239967 A1 | 9/2013 | Jafari et al. |
| 2013/0255682 A1 | 10/2013 | Jafari et al. |
| 2013/0255685 A1 | 10/2013 | Jafari et al. |
| 2013/0276788 A1 | 10/2013 | Masic |
| 2013/0283197 A1 | 10/2013 | Skidmore |
| 2013/0284172 A1 | 10/2013 | Doyle et al. |
| 2013/0284173 A1 | 10/2013 | Masic et al. |
| 2013/0284177 A1 | 10/2013 | Li et al. |
| 2014/0000606 A1 | 1/2014 | Doyle et al. |
| 2014/0012150 A1 | 1/2014 | Milne et al. |
| 2014/0123979 A1 | 5/2014 | Doyle et al. |
| 2014/0182590 A1 | 7/2014 | Platt et al. |
| 2014/0224250 A1 | 8/2014 | Sanchez et al. |
| 2014/0251328 A1 | 9/2014 | Graboi et al. |
| 2014/0261409 A1 | 9/2014 | Dong et al. |
| 2014/0261410 A1 | 9/2014 | Sanchez et al. |
| 2014/0261424 A1 | 9/2014 | Doyle et al. |
| 2014/0276176 A1 | 9/2014 | Winter |
| 2014/0373845 A1 | 12/2014 | Dong |
| 2015/0034082 A1 | 2/2015 | Kimm et al. |
| 2015/0039045 A1* | 2/2015 | Ni .................. A61B 5/0826 607/42 |
| 2014/0034054 A1 | 5/2015 | Angelico et al. |

OTHER PUBLICATIONS

7200 Ventilatory System: Addendum/Errata. Nellcor Puritan Bennett, Part No. 4-023576-00, Rev. A, Apr. 1998, pp. 1-32.

800 Operator's and Technical Reference Manual. Series Ventilator System, Nellcor Puritan Bennett, Part No. 4-070088-00, Rev. L, Aug. 2010, pp. 1-476.

840 Operator's and Technical Reference Manual. Ventilator System, Nellcor Puritan Bennett, Part No. 4-075609-00, Rev. G, Oct. 2006, pp. 1-424.

* cited by examiner

DETECTION OF EXPIRATORY AIRFLOW LIMITATION IN VENTILATED PATIENT

INTRODUCTION

A ventilator is a device that mechanically helps patients breathe by replacing some or all of the muscular effort required to inflate and deflate the lungs. In recent years, there has been an accelerated trend towards an integrated clinical environment. That is, medical devices are becoming increasingly integrated with communication, computing, and control technologies. As a result, modern ventilatory equipment has become increasingly complex, providing for detection, monitoring, and evaluation of myriad ventilatory parameters during ventilation of a patient.

For example, patients with advanced stages of chronic obstructive pulmonary disease (COPD), which is characterized by chronic inflammation and thickening of the airways, have difficulty exhaling due to a constriction of the lung bronchioles shortly after the start of exhalation (referred to as expiratory airflow limitation). It would be advantageous to detect when a patient is experiencing expiratory airflow limitation in order to provide appropriate ventilatory management.

Detection of Expiratory Airflow Limitation in Ventilated Patient

This disclosure describes systems and methods for monitoring and evaluating data associated with ventilatory parameters to detect expiratory airflow limitation in a ventilated patient. For example, a ventilator may monitor flow and/or pressure during ventilation of the patient. Based on the flow and/or pressure measurements, or ventilatory data derived therefrom, the ventilator may calculate expiratory airflow resistance (hereinafter referred to as "expiratory resistance"). Moreover, the ventilator may trend expiratory resistance over time to produce an expiratory resistance waveform. In embodiments, the ventilator may calculate the slope of the resistance waveform during an initial part of exhalation. If the slope of the expiratory resistance waveform during the initial part of exhalation breaches a defined slope threshold, the ventilator may determine that the patient exhibits expiratory airflow limitation. Alternatively, if the slope of the expiratory resistance waveform during the initial part of exhalation does not breach the defined slope threshold, the ventilator may determine that the patient does not exhibit expiratory airflow limitation.

According to embodiments, a ventilator-implemented method is provided for determining whether a ventilated patient exhibits an expiratory airflow limitation. The method comprises monitoring ventilatory parameters and trending airflow resistance over time during an expiratory phase to produce a resistance waveform. The method also comprises calculating a slope of the resistance waveform, comparing the slope of the resistance waveform to a defined slope threshold, and determining that the patient exhibits an expiratory airflow limitation if the slope of the resistance waveform is greater than or equal to the defined slope threshold.

According to additional embodiments, a system is provided that comprises at least one processor and at least one memory communicatively coupled to the at least one processor and containing instructions that, when executed by the at least one processor, cause a controller to determine whether the ventilated patient exhibits expiratory airflow limitation. The controller comprises a monitoring module for monitoring ventilatory parameters and an expiratory resistance detection module for calculating airflow resistance during an expiratory phase and trending airflow resistance over time during the expiratory phase to produce a resistance waveform. The controller further comprises an expiratory airflow limitation detection module for calculating a slope of the resistance waveform, comparing the slope of the resistance waveform to a defined slope threshold, and determining that the patient exhibits an expiratory airflow limitation if the slope of the resistance waveform is greater than or equal to the defined slope threshold.

According to additional embodiments, a computer storage device is provided that stores instructions, which when executed by a processor cause a controller to determine whether a ventilated patient exhibits an expiratory airflow limitation. The controller comprises a monitoring module for monitoring ventilatory parameters and an expiratory resistance detection module for trending airflow resistance over time during an expiratory phase to produce a resistance waveform. The controller further comprises an expiratory airflow limitation detection module for calculating a slope of the resistance waveform, comparing the slope of the resistance waveform to a defined slope threshold, and determining that the patient exhibits an expiratory airflow limitation if the slope of the resistance waveform is greater than or equal to the defined slope threshold.

These and various other features as well as advantages which characterize the systems and methods described herein will be apparent from a reading of the following detailed description and a review of the associated drawings. Additional features are set forth in the description which follows, and in part will be apparent from the description, or may be learned by practice of the technology. The benefits and features of the technology will be realized and attained by the structure particularly pointed out in the written description and claims hereof as well as the appended drawings.

It is to be understood that both the foregoing general description and the following detailed description are exemplary and explanatory and are intended to provide further explanation of the claims.

BRIEF DESCRIPTION OF THE DRAWINGS

The following drawing figures, which form a part of this application, are illustrative of described technology and are not meant to limit the scope of the claims in any manner, which scope shall be based on the claims appended hereto.

DETAILED DESCRIPTION

Although the techniques introduced above and discussed in detail below may be implemented for a variety of medical devices, the present disclosure will discuss the implementation of these techniques for use in a mechanical ventilator system. The reader will understand that the technology described in the context of a ventilator system could be adapted for use with other therapeutic equipment.

According to embodiments, a ventilator may be configured to detect expiratory airflow limitation in a ventilated patient. For example, the ventilator may detect expiratory airflow limitation in a ventilated patient based on evaluating, inter alia, ventilatory data (e.g., flow, volume, pressure, compliance, ventilator setup data, etc.), patient data (e.g., a patient body weight, a patient diagnosis, a patient gender, a patient age, etc.), and/or any suitable protocol, equation, etc. Specifically, based on the ventilatory data, the ventilator may calculate expiratory resistance, e.g., expiratory lung resistance. Moreover, the ventilator may trend expiratory resistance over time to produce an expiratory resistance waveform. In other embodiments, the ventilator may calculate the slope of the expiratory resistance waveform during an initial part of exhalation, e.g., from about the first 100 to 300 milliseconds (ms) of exhalation.

If the slope of the expiratory resistance waveform during the initial part of exhalation breaches a defined slope of resistance threshold (slope_$R_L$, threshold) (e.g., 100 cmH$_2$O/l/s/s), the ventilator may determine that the patient exhibits expiratory airflow limitation. Alternatively, if the slope of the expiratory resistance waveform during the initial part of exhalation does not breach the slope_$R_L$ threshold, the ventilator may determine that the patient does not exhibit expiratory airflow limitation. In some embodiments, the ventilator may further determine if the slope of the expiratory resistance waveform during the initial part of exhalation breaches the slope_$R_L$ threshold for a threshold number of breaths (or a threshold percentage of breaths). In this case, if the slope of the expiratory resistance waveform during the initial part of exhalation breaches the slope_$R_L$ threshold for a threshold number of breaths (or a threshold percentage of breaths), the ventilator may determine that the patient exhibits expiratory airflow limitation. Alternatively, if the slope of the expiratory resistance waveform during the initial part of exhalation does not breach the slope_$R_L$ threshold for the threshold number of breaths (or a threshold percentage of breaths), the ventilator may determine that the patient does not exhibit expiratory airflow limitation.

These and other embodiments will be discussed in further detail with reference to the following figures.

Figure 1:
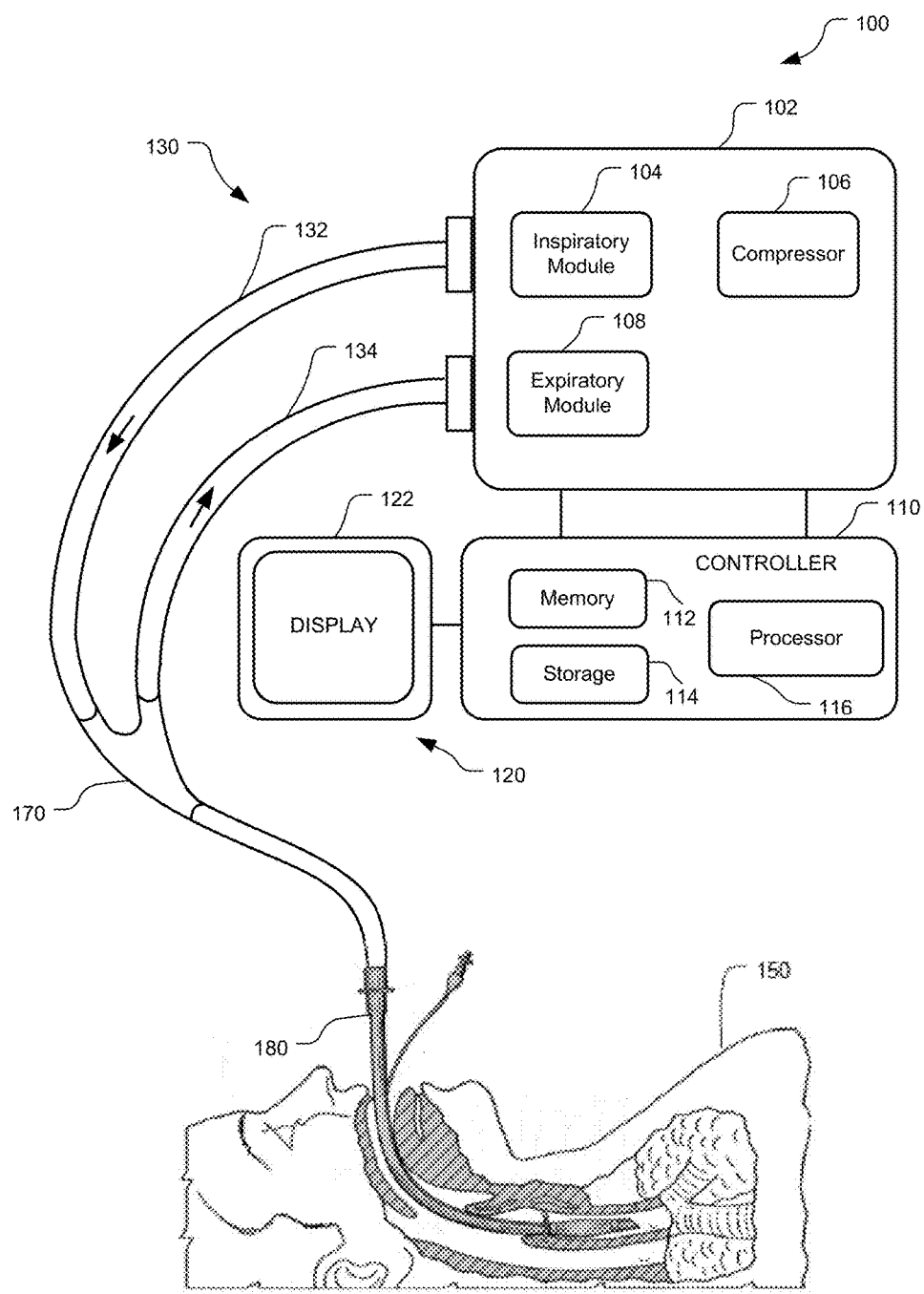
FIG. 1 is a diagram illustrating an embodiment of an exemplary ventilator connected to a human patient.

FIG. 1 is a diagram illustrating an embodiment of an exemplary ventilator connected to a human patient.

FIG. 1 illustrates ventilator 100 connected to a human patient 150 via a double-limb patient circuit connected to an artificial airway. Ventilator 100 includes a pneumatic system 102 (also referred to as a pressure generating system 102) for circulating breathing gases to and from patient 150 via the ventilation tubing system 130, which couples the patient to the pneumatic system 102 via an invasive (e.g., endotracheal tube, as shown) or a non-invasive (e.g., nasal mask, not shown) patient interface.

Ventilation tubing system 130 (also referred to as a patient circuit) may be a two-limb (shown) or a one-limb circuit (not shown) for carrying gases to and from the patient 150. In a two-limb embodiment, a fitting, typically referred to as a "wye-fitting" 170, may be provided to couple an endotracheal tube 180 (alternatively a tracheostomy tube 180 or a mask 180 may be employed) to an inspiratory limb 132 and an expiratory limb 134 of the ventilation tubing system 130.

Pneumatic system 102 may be configured in a variety of ways. In the present example, system 102 includes an inspiratory module 104 coupled with the inspiratory limb 132 and an expiratory module 108 coupled with the expiratory limb 134. Compressor 106 or other source(s) of pressurized gases (e.g., air, oxygen, and/or helium) is coupled with inspiratory module 104 to provide a gas source for ventilatory support via inspiratory limb 132.

The pneumatic system 102 may include a variety of other components, including mixing modules, valves, sensors, tubing, accumulators, filters, etc. Controller 110 is operatively coupled with pneumatic system 102, signal measurement and acquisition systems, and an operator interface 120 that may enable an operator to interact with the ventilator 100 (e.g., change ventilator settings, select operational modes, view monitored parameters, etc.). Controller 110 may include memory 112, one or more processors 116, storage 114, and/or other components of the type commonly found in command and control computing devices. In the depicted example, operator interface 120 includes a display 122 that may be touch-sensitive and/or voice-activated, enabling the display to serve both as an input and output device.

The memory 112 includes non-transitory, computer-readable storage media that stores software (or computer-readable instructions) that, when executed by the processor 116, controls the operation of the ventilator 100. In an embodiment, the memory 112 includes computer storage devices, e.g., one or more solid-state storage devices such as flash memory chips. In an alternative embodiment, the memory 112 may be mass storage connected to one or more processors 116 through a mass storage controller (not shown) and a communications bus (not shown). Although the description of computer-readable media contained herein refers to a solid-state storage, it should be appreciated by those skilled in the art that computer-readable storage media can be any available media that can be accessed by the one or more processors 116. That is, computer-readable storage media includes non-transitory, volatile and non-volatile, removable and non-removable media implemented in any method or technology for storage of information such as computer-readable instructions, data structures, program modules or other data. For example, computer-readable storage media includes RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by the computer.

Communication between components of the ventilatory system or between the ventilatory system and other therapeutic equipment and/or remote monitoring systems may be conducted over a distributed network, as described further herein, via wired or wireless means. Further, the present methods may be configured as a presentation layer built over the TCP/IP protocol. TCP/IP stands for "Transmission Control Protocol/Internet Protocol" and provides a basic communication language for many local networks (such as intranets or extranets) and is the primary communication language for the Internet. Specifically, TCP/IP is a bi-layer protocol that allows for the transmission of data over a network. The higher layer, or TCP layer, divides a message into smaller packets, which are reassembled by a receiving TCP layer into the original message. The lower layer, or IP layer, handles addressing and routing of packets so that they are properly received at a destination.

Figure 2:
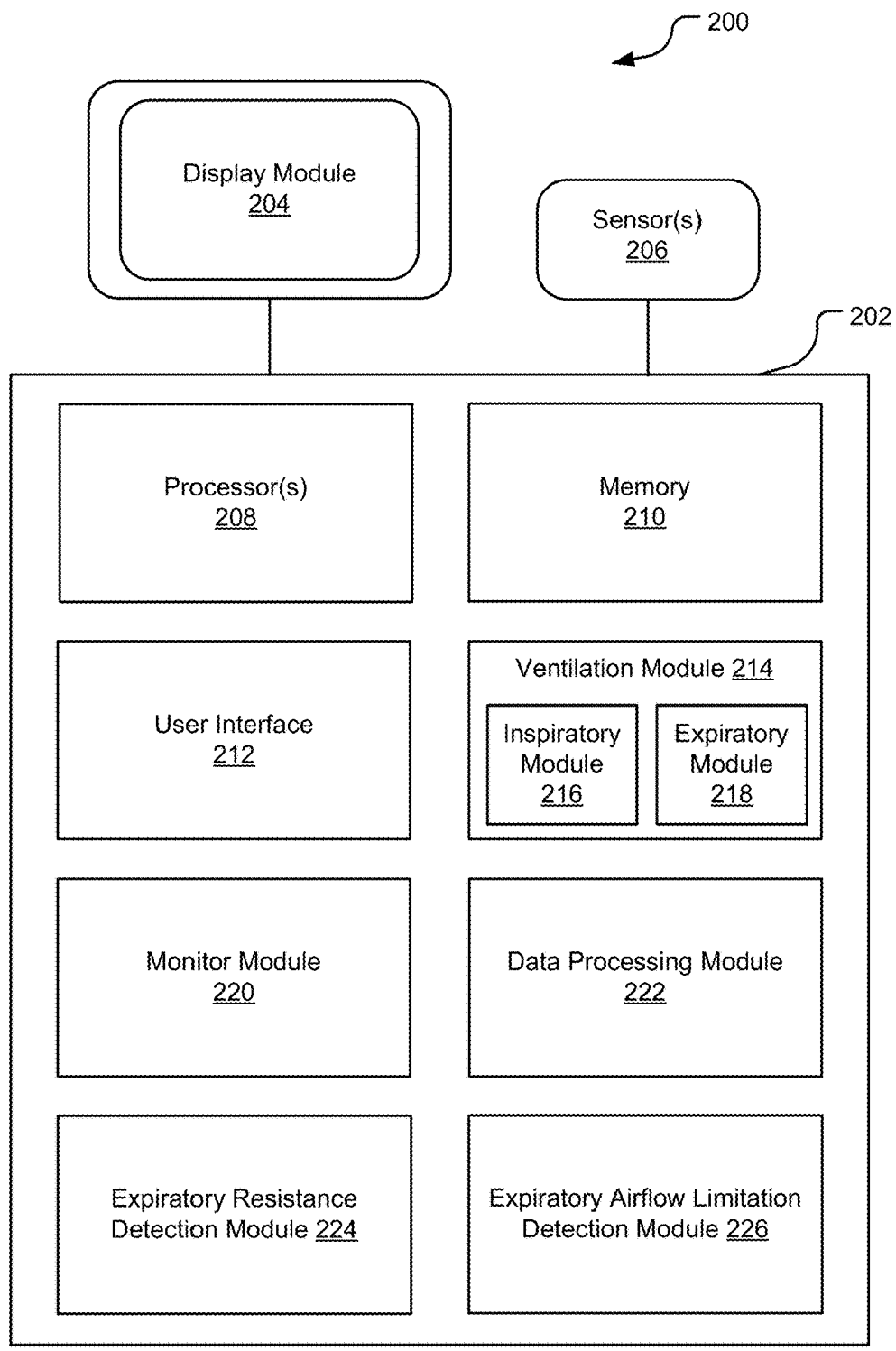
FIG. 2 is a block-diagram illustrating an embodiment of a ventilatory system for determining whether a ventilated patient exhibits expiratory airflow limitation.

FIG. 2 is a block-diagram illustrating an embodiment of a ventilatory system for determining whether a ventilated patient exhibits expiratory airflow limitation.

Ventilator system 200 includes ventilator 202 with its various modules and components. That is, ventilator 202 may further include a memory 210, one or more processors 208, user interface 212, and ventilation module 214 (which may further include an inspiratory module 216 and an expiratory module 218). Memory 210 is defined as described above for memory 112. Similarly, the one or more processors 208 are defined as described above for one or more processors 116. Processors 208 may further be configured with a clock whereby elapsed time may be monitored by the ventilator system 200.

The ventilator system 200 may also include a display module 204 communicatively coupled to ventilator 202. Display module 204 may provide various input screens, for receiving clinician input, and various display screens, for presenting data and information to the clinician. The display module 204 is configured to communicate with user interface 212 and may include a graphical user interface (GUI). The GUI may be an interactive display, e.g., a touch-sensitive screen or otherwise, and may provide various windows and elements for receiving input and interface command operations. Alternatively, other suitable means of communication with the ventilator 202 may be provided, for instance by a wheel, keyboard, mouse, or other suitable interactive device. Thus, user interface 212 may accept commands and input through display module 204. Display module 204 may also provide information in the form of various data regarding the physical condition of a patient and/or a prescribed respiratory treatment as well as the operational state of the ventilator. For example, the data may include collected, processed, or derived values for one or more ventilatory parameters. The information may be based on data collected by one or more sensors 206 associated with monitor module 220 or data derived or otherwise processed by data processing module 222, and the information may be displayed to the clinician in the form of graphs, waveform representations, pie graphs, or other suitable forms of graphic display.

The ventilator system 200 may also include one or more sensors 206 communicatively coupled to ventilator 202. Sensors 206 may communicate with various components of ventilator 202, e.g., ventilation module 214, monitor module 220, data processing module 222, expiratory resistance detection module 224, expiratory airflow limitation detection module 226, or any other suitable components and/or modules. Sensors 206 may collect data indicative of pressure and/or flow, for example. Sensors 206 may be placed in any suitable location, e.g., within the ventilatory circuitry or other devices communicatively coupled to the ventilator. For example, sensors may be affixed to the ventilatory tubing, may be imbedded in the tubing itself, or may be affixed to the patient. According to some embodiments, sensors may be provided at or near the lungs (or diaphragm) for detecting a pressure in the lungs. Additionally or alternatively, sensors may be affixed or imbedded in or near wye-fitting 170 and/or patient interface 180, as described above. Sensors may further be provided within components or modules of ventilator 202. For example, sensors may be coupled to the inspiratory and/or expiratory modules for detecting changes in, for example, circuit pressure and/or flow.

Sensors 206 may include pressure transducers that may detect changes in circuit pressure (e.g., electromechanical transducers including piezoelectric, variable capacitance, or strain gauge). Sensors 206 may further include various flowmeters for detecting airflow (e.g., differential pressure pneumotachometers, turbine flowmeters, etc.). Alternatively, sensors may utilize optical or ultrasound techniques for measuring changes in ventilatory parameters. Indeed, any sensory device useful for monitoring changes in measurable parameters during ventilatory treatment may be employed in accordance with embodiments described herein.

Ventilation module 214 may oversee ventilation of a patient according to prescribed ventilatory settings. By way of general overview, the basic elements impacting ventilation during inspiration may be described by the following simplified ventilatory equation (also known as the Equation of Motion):

$$P_{APPL}=[R_{TOT}*Q]+[V_T/C]-P_{MUS}$$

Here it is understood that $P_{APPL}$ is an inflation pressure (generally expressed in $cmH_2O$) applied externally to the respiratory system, i.e., via patient interface 180 as depicted in FIG. 1, and that $P_{MUS}$ represents the neuromuscular pressure-generating system within the patient's thorax. Thus, during normal breathing $P_{APPL}$=zero and all the work of inspiration is supplied by the patient's respiratory-muscles. And conversely during anesthesia, $P_{MUS}$ is nominally quiescent and all of the work of inspiration is supplied by a breathing device. However, with partial ventilatory support, both $P_{APPL}$ and $P_{MUS}$ will be non-zero during inspiration. In this equation $R_{TOT}$ (generally expressed as $cmH_2O/l/s$) represents the airflow-resistive elements through which gas must flow (Q) (generally expresses as l/min or ml/min or alternately mL/min) to reach the capacitive element C (generally expressed as $ml/cmH_2O$ or alternately $mL/cmH_2O$), whose value is assumed to remain nominally constant during ventilation. $V_T$ represents accumulated lung volume as generated by the forcing functions $P_{APPL}$ and/or $P_{MUS}$. As depicted in FIG. 1, $R_{TOT}=R_T$ (artificial airway)+$R_L$ (lung). It is further understood that in a ventilator-patient system such as the one depicted in FIG. 1, $P_{APPL}$ and/or $P_{MUS}$ will be continuous functions of time from beginning inspiration until inspiration ends. Therefore, if pressures and flows are measured/monitored/referenced to the $P_Y$ (wye) position 170 in FIG. 1, the waveforms/time traces will mirror those shown in FIGS. 3 and 6. Data representative of any of the above ventilatory parameters may be measured, collected, processed, calculated and/or estimated by one or more components of ventilator system 200.

In embodiments, the ventilator-applied inflation pressure, $P_{APPL}$, may be measured by the ventilator by any suitable means and may be representative of the positive pressure existing at the patient airway, $P_Y$. In embodiments, $P_{APPL}$ is uninfluenced by elements on the ventilator side of the patient circuit and reflects the pressure existing at the wye interface (i.e., $P_Y$ at wye 170 in FIG. 1). For example, $P_{APPL}$ may be measured by one or more pressure transducers placed at any suitable location, e.g., affixed to or imbedded in the ventilatory tubing (or patient circuit), affixed to or imbedded in or near wye-fitting and/or patient interface, or provided within components or modules of the ventilator, such as the inspiratory and/or expiratory modules. In embodiments, $P_{APPL}$ may be measured in any suitable location by any suitable device, e.g., by a sensor associated with the wye fitting, by sensors associated with the expiratory-valve module, and/or by sensors associated with the inspiratory module and safety valve.

Volume refers to the amount of gas delivered to a patient's lungs, usually in liters (l). Flow refers to a change in volume over time ($Q=\Delta V/\Delta t$). Flow is generally expressed in liters per minute (l/min) and, depending on whether gases are flowing into or out of the lungs, flow may be referred to as inspiratory flow or expiratory flow, respectively. According to embodiments, the ventilator may control the rate of delivery of gases to the patient, i.e., inspiratory flow, and may control the rate of release of gases from the patient, i.e., expiratory flow.

As may be appreciated, volume and flow are closely related. That is, where flow is known or regulated, volume may be derived based on elapsed time. In embodiments, flow may be measured by any suitable means, e.g., via one or more flow sensors associated with the patient circuit, patient wye, or any ventilator component or module, e.g., the inspiratory or expiratory module. In some embodiments, the flow signal received from the sensors may be compensated for humidity, or other consideration, to provide net flow, $Q_{NET}$, where $Q_{NET}$ represents an estimate of the true flow entering and leaving the patient's lungs during inspiration and exhalation, respectively. As with other ventilatory parameters, $Q_{NET}$ may be trended over time to provide a net flow waveform. Moreover, volume (or net volume) may be derived by integrating the flow (or net flow) waveform. According to embodiments, a tidal volume, $V_T$, may be delivered upon reaching a set inspiratory time ($T_I$) at set inspiratory flow. Alternatively, set $V_T$ and set inspiratory flow may determine the amount of time required for inspiration, i.e., $T_I$.

Additional ventilatory parameters that may be measured and/or derived may include compliance and resistance, which refer to the load against which the patient and/or the ventilator must work to deliver gases to the lungs. Generally, compliance refers to a relative ease with which something distends and is the inverse of elastance, which refers to the tendency of something to return to its original form after being deformed. As related to ventilation, compliance refers to the lung volume achieved for a given amount of delivered pressure ($C=\Delta V/\Delta P$). To detect changes in compliance, one variable may be held constant at the end of inspiration and changes in the other variable may be utilized to determine whether compliance has changed and in what direction. Some lung diseases (e.g., acute respiratory distress syndrome (ARDS)) may decrease compliance and, thus, require increased pressure to inflate the lungs. Alternatively, other lung diseases may increase compliance, e.g., emphysema, and may require less pressure to inflate the lungs.

Resistance refers to frictional forces that resist airflow, e.g., due to synthetic structures (e.g., endotracheal tube, etc.), anatomical structures (e.g., trachea and major bronchiolar tree, small bronchi and terminal bronchioles, and terminal airways, etc.), or viscous tissues of the lungs (e.g., alveolar tissues). Resistance is highly dependent on the diameter of the airway. In fact, decreasing the diameter of the airway results in an exponential increase in resistance (e.g., two-times reduction of diameter increases resistance by sixteen times). As may be appreciated, resistance may increase due to a restriction of the airway that is the result of, inter alia, bronchial constriction, increased secretions, bronchial edema, mucous plugs, bronchospasm, and/or kinking of the patient interface (e.g., invasive endotracheal or tracheostomy tubes).

Although the Equation of Motion equation, briefly described above, provides a satisfactory model for understanding pressures and flows during the inspiratory phase of a breath in a patient-ventilator system, an alternate approach has been selected to meet the needs of this disclosure. At the end of the inspiratory phase just before the beginning of exhalation the lung receives a volume, $V_T$. Assuming a passive exhalation and the cessation of either of the active agents of inflation, $P_{APPL}$ or $P_{MUS}$, the recoil pressure of the lung becomes manifest and equal to $V_T/C$. It is not germane to this disclosure how $V_T$ or C are determined but the literature contains numerous references by which these variables may be measured, calculated, or estimated.

Figure 3:
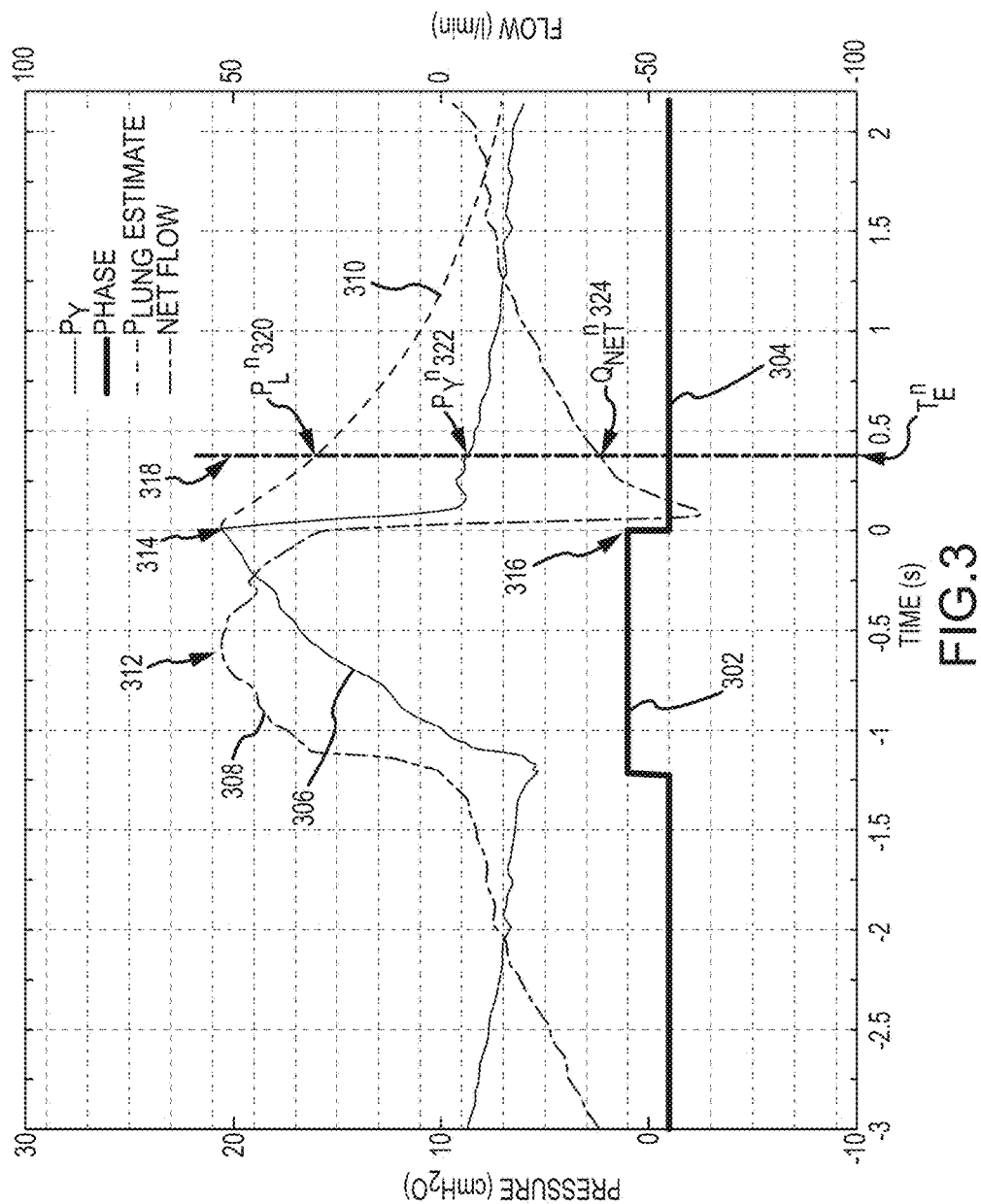
FIG. 3 is a graph illustrating pressure and flow waveforms for an example patient who does not exhibit expiratory airflow limitation.

With reference to FIG. 3, it may be appreciated that during passive exhalation $P_L''=V_T''/C$ at any value of $T_E''$. Also known is that the total resistance impeding expiratory flow is given by $R_{TOT}''=R_L''+R_T''$. With $P_L''$ determined and $P_Y''$ monitored it is appreciated that for any $T_E''$, $R_{TOT}''=(P_L''-P_Y'')/Q''$, where $Q''$ is taken as $Q_{NET}''$. Once $R_{TOT}''$ is known, the value of $R_L''$ is found from $R_L''=R_{TOT}''-R_T''$, where $R_T''$ is calculated using a look-up table or other suitable method.

Resistance is generally expressed in centimeters of water per liters per second (i.e., $cmH_2O/L/s$ or $cmH_2O/l/s$). $\Delta P_L$ refers to the driving pressure necessary to overcome resistive forces, including both lung resistance ($R_L$) and tube resistance ($R_T$), and during exhalation may be calculated as the difference between $P_Y$ and $P_L$. In embodiments, $R_L$ may be estimated by calculating the total resistance and subtracting $R_T$. For a significant percentage of patients with expiratory airflow limitation, $R_L$ may be near normal immediately after the beginning of exhalation and then increase in value as exhalation continues due to constriction of the bronchioles. Accordingly, for a patient with expiratory airflow limitation, $\Delta P$ may be higher during an initial part of exhalation than during inspiration and/or flow may be lower during an initial part of exhalation than during inspiration. In embodiments, the calculations for resistance above are applicable for calculating expiratory lung resistance.

Ventilation module 214 may further include an inspiratory module 216 configured to deliver gases to the patient according to prescribed ventilatory settings. Specifically, inspiratory module 216 may correspond to the inspiratory module 104 or may be otherwise coupled to source(s) of pressurized gases (e.g., air, oxygen, and/or helium), and may deliver gases to the patient. Inspiratory module 216 may be configured to provide ventilation according to various ventilatory modes and/or breath types, e.g., via volume-targeted, pressure-targeted, spontaneous, mandatory, or via any other suitable type of ventilation.

For example, according to embodiments, the inspiratory module 216 may provide ventilation via a form of volume ventilation. Volume ventilation refers to various forms of volume-targeted ventilation that regulate volume delivery to the patient. For example, in volume-cycled ventilation, an end of inspiration is determined based on monitoring the volume delivered to the patient. For volume-cycled ventilation, when the delivered volume is equal to the prescribed $V_T$, the ventilator may initiate exhalation. According to alternative embodiments, the inspiratory module 216 may provide ventilation via a form of pressure ventilation. Pressure-targeted ventilation may be provided by regulating the pressure delivered to the patient in various ways. For example, during pressure ventilation, the ventilator may maintain a pressure waveform at the mouth, $P_{APPL}$, until an inspiratory pressure ($P_I$) is reached, at which point the ventilator may initiate exhalation or until both a desired inspiratory pressure ($P_I$) and a desired inspiratory time ($T_I$) have been attained.

In some embodiments, the inspiratory module 216 may provide pressure-targeted ventilation via a proportional assist type of ventilation. In this case, the ventilator delivers breathing gases to a spontaneously-breathing patient in synchrony with the patient's effort to reduce the patient's work of inspiration (which comprises the greater part of the WOB). The patient's WOB is essentially dependent on the load against which the patient inhales, including patient respiratory characteristics (i.e., anatomical resistance and compliance) and the resistance associated with the synthetic structures (e.g., endotracheal or tracheostomy tube, etc.). In embodiments, during proportional assist ventilation, the ventilator may deliver a real-time, calculated inspiratory target pressure to the patient airway that is a function of monitored flow, a clinician-selected amount of support pressure, a clinician-selected positive end-expiratory pressure (PEEP), an estimate of the patient's resistance and elastance, and a calculation of the tube resistance (dependent on the internal diameter of the endotracheal or tracheostomy tube). In other embodiments the ventilator may algorithmically determine the patient's resistance and compliance, control the support pressure, and manage other aspects of the breathing algorithm.

Ventilation module 214 may further include an expiratory module 218 configured to release gases from the patient's lungs according to prescribed ventilatory settings. Expiratory module 218 may correspond to expiratory module 108 or may otherwise be associated with and/or controlling an expiratory valve for releasing gases from the patient. By way of general overview, a ventilator may initiate exhalation based on lapse of an inspiratory time setting ($T_I$) or other cycling criteria set by the clinician or derived from ventilator settings (e.g., detecting delivery of prescribed $V_T$ or prescribed inspiratory pressure based on a reference trajectory). Upon initiating the expiratory phase, expiratory module 218 may allow the patient to exhale by controlling the expiratory valve.

As should be appreciated, with reference to the Equation of Motion, ventilatory parameters are highly interrelated and, according to embodiments, may be directly or indirectly monitored. For example, the sensors may provide raw data to the monitor module 220. The raw data may further be provided to the data processing module 222 for processing and/or deriving (e.g., by calculation, estimation, etc.) ventilatory data. That is, parameters may be directly monitored by one or more sensors, as described above, or may be indirectly monitored by derivation according to the Equation of Motion or other equation, algorithm, etc.

Ventilator 202 may further include a data processing module 222. As noted above, sensors may collect data regarding various ventilatory parameters. A ventilatory parameter refers to any factor, characteristic, or measurement associated with the ventilation of a patient, whether monitored by the ventilator or by any other device. Sensors may further transmit collected data to the monitor module 220 and/or the data processing module 222. According to embodiments, the data processing module may 222 be configured to collect data regarding some ventilatory parameters, to derive data regarding other ventilatory parameters, and/or to transform the collected and/or derived ventilatory data into digital or graphical data for display to the clinician and/or other modules of the ventilatory system. According to embodiments, the collected, derived digital, and/or graphically transformed data may be generally defined as ventilatory data.

For example, according to embodiments, data processing module 222 may be configured to monitor flow and/or pressure. As may be appreciated, flow decreases as resistance increases, making it more difficult to pass gases into and out of the lungs (i.e., $Q=\Delta P/R_{TOT}$). According to embodiments, an increase in $\Delta P$ or a decrease in flow may be indicative of an increase in resistance, while a decrease in $\Delta P$ or an increase in flow may be indicative of a decrease in resistance (i.e., $R_{TOT}=\Delta P/Q$). For example, increased resistance may be observed in patients with obstructive disorders, such as COPD, asthma, etc.

Ventilator 202 may further include expiratory resistance detection module 224. According to embodiments, expiratory resistance detection module 224 may evaluate the ventilatory data to calculate expiratory resistance for the patient. The expiratory resistance detection module 224 may further trend expiratory resistance values for the patient via any suitable means. "Trending," as used herein, means collecting and/or calculating data over a plurality of breaths (or at predetermined intervals of time). For example, $P_L$, $P_Y$, $\Delta P$ and/or flow may be trended over time, based on data collected, processed and/or derived by the ventilator. Moreover, the resistance detection module 224 may trend $R_{TOT}$, $R_L$ and/or $R_T$ over time based on calculations associated with the pressure and/or flow waveforms, as described above. Additionally, upon trending $R_{TOT}$, $R_L$ and/or $R_T$ over time, the ventilator 202 may produce and/or display waveforms for one or more of $R_{TOT}$, $R_L$ and/or $R_T$.

Ventilator 202 may further include an expiratory airflow limitation detection module 226 for determining whether a ventilated patient has expiratory airflow limitation. For purposes of this disclosure, "expiratory airflow limitation" refers to a difficulty in exhaling. For example, for patients with COPD, resistance may be relatively normal during inspiration but may be significantly higher during exhalation. Difficulty exhaling, or expiratory airflow limitation, results when the intra-thoracic pressure (which is high at the end of inspiration) acts to compress the bronchioles shortly after the start of exhalation.

In order to determine whether a patient has expiratory airflow limitation, the expiratory airflow limitation detection module 226 may calculate a rate of change (or slope) of resistance for the patient. In some embodiments, the ventilator may calculate the slope of total resistance, $R_{TOT}$. In other embodiments, the expiratory airflow limitation detection module 226 may calculate the slope of lung resistance, $R_L$. As noted above, total resistance is equal to $\Delta P$ divided by flow ($R_{TOT}=\Delta P/Q$). Total resistance is further equal to tube resistance, $R_T$, plus lung resistance, $R_L$ ($R_{TOT}=R_T+R_L$). Accordingly, lung resistance, $R_L$, is equal to $\Delta P$ divided by flow minus tube resistance, $R_T$ ($R_L=[\Delta P/Q]-R_T$). In embodiments, as described above, $R_L$ may be trended over time to result in a $R_L$ waveform. The slope of the $R_L$ waveform may be calculated over a period of time, e.g., between about 0.100 and 0.300 s (or 100 and 300 ms) after exhalation begins.

In further embodiments, expiratory airflow limitation detection module 226 may compare the slope of the $R_L$ waveform (or the $R_{TOT}$ waveform) to a defined slope of resistance threshold (slope_$R_L$ threshold) in order to determine whether the patient has expiratory airflow limitation. In embodiments, the slope_$R_L$ threshold may be equal to about 100 cmH$_2$O/l/s/s. In other embodiments, the slope_$R_L$ threshold may be equal to another suitable value based on a statistical evaluation of COPD patients or otherwise. In embodiments, if the slope of the $R_L$ waveform for a patient is greater than or equal to the slope_$R_L$ threshold, the expiratory airflow limitation detection module 226 may determine that the patient has expiratory airflow limitation. Alternatively, if the slope of the $R_L$ waveform for a patient is less than the slope_$R_L$ threshold, the expiratory airflow limitation detection module 226 may determine that the patient does not have expiratory airflow limitation.

In some embodiments, the expiratory airflow limitation detection module 226 may determine that the patient has expiratory airflow limitation based on evaluating the slope of the $R_L$ waveform (or the $R_{TOT}$ waveform) over a plurality of breaths. In this case, the expiratory airflow limitation detection module 226 may determine that the patient has expiratory airflow limitation if the slope of the $R_L$ waveform for the patient is greater than or equal to the slope_$R_L$ threshold for a threshold number of breaths (or a threshold percentage of breaths, etc.). For example, the expiratory airflow limitation detection module 226 may determine that the patient has expiratory airflow limitation if the slope of the $R_L$ waveform for the patient is greater than or equal to the slope_$R_L$ threshold for 4 of 5 consecutive breaths, or for 5 of 10 consecutive breaths, or in 60% of breaths. In this example, the expiratory airflow limitation detection module 226 may determine that the patient does not have expiratory airflow limitation when the slope of the $R_L$ waveform for the patient is greater than or equal to the slope_$R_L$ threshold for less than the threshold number of breaths (or the threshold percentage of breaths).

Upon determining that a patient has expiratory airflow limitation, the ventilator 202 may recommend or automatically adjust ventilatory settings in order to provide appropriate ventilation. For example, appropriate changes may include, but are not limited to, an adjusted WOB estimation (e.g., using a default value for R) for the proportional assist ventilation breath type, a lower respiratory rate (resulting in a higher expiratory time ($T_E$) for complete exhalation of gases), an alternate waveform setting for mandatory breath types, etc.

Ventilator system 200 is exemplary and explanatory and is intended to provide further explanation of the claims. However, it is contemplated that ventilator 200 may have more or fewer components within the spirit of the present disclosure and description of the various components and modules of ventilator 200 is not intended to be limiting.

FIG. 3 is a graph illustrating pressure and flow waveforms for an example patient who does not exhibit expiratory airflow limitation.

FIG. 3 provides a graphical representation of pressure and flow waveforms over time (in seconds) during an inspiratory phase 302 and an expiratory phase 304 of a breath cycle for a ventilated patient. A pressure ($P_Y$) measured during inspiration 302 is an inflation pressure ($P_{APPL}$) if it exceeds the initial end-exhalation pressure of the previous breath. That is, the pressure ($P_Y$) waveform 306 during inspiratory phase 302 is equivalent to $P_{APPL}$ as defined in this application. Thus, in embodiments, while $P_{APPL}$ properly refers to an applied pressure during inspiration, $P_Y$ may be used to refer to pressure readings during either inspiration or expiration. An inspiratory-expiratory pressure ($P_Y$) waveform 306 is presented in units of centimeters of water (cmH$_2$O), a net flow ($Q_{NET}$) waveform 308 is presented in units of liters per minute (l/min), and an estimated lung pressure ($P_E$) waveform 310 is presented in units of cmH$_2$O.

As illustrated by net flow ($Q_{NET}$) waveform 308, $Q_{NET}$ increases to a peak flow 312 around a middle part of inspiration and then decreases for the remainder of inspiration. Conceptually, the ventilator terminates inspiratory flow ($Q_{NET}$) at event 316. Thereafter, the ventilator enters the expiratory phase in which $Q_{NET}$ is assigned negative values. Immediately after the beginning of exhalation 316, $Q_{NET}$ increases sharply to about −60 l/min or more as the direction of the flow of gases switches from entering the lungs to exiting the lungs. Note that gas flow is identified as a negative value because gases are exiting the lungs; however, the rate of exit is high (i.e., increases) just as exhalation begins. Thereafter, as exhalation progresses, the flow of air exiting the lungs gradually decreases to about zero l/min at the end of exhalation, at which point equilibrium is reached and gas no longer exits the lungs.

As illustrated by pressure ($P_Y$) waveform 306, $P_{APPL}$ increases to a peak pressure 314 at the end of inspiration. At the beginning of exhalation 316, $P_Y$ ($P_{APPL}$ technically transitions to $P_Y$ at 316) decreases sharply in the first few tenths of a second (e.g., first 100 ms) of exhalation when the ventilator discontinues positive pressure to the patient airway and the direction of gas flow switches from entering to exiting the patient's lungs. Thereafter, $P_Y$ stabilizes and, as exhalation progresses, $P_Y$ decreases gradually toward the clinician-set PEEP level (in this example, about 5 cmH$_2$O). In embodiments, PEEP is an amount of end-expiratory pressure that is maintained in the lungs at the end of exhalation to prevent collapse of the alveoli and/or promote gas exchange. PEEP may be set on a per patient basis and may include any appropriate value between nominally zero to five cmH$_2$O and 10 to 20 or more cmH$_2$O.

As illustrated by $P_L$ waveform 310, $P_L$ is roughly equal to peak pressure 314 at the beginning of exhalation 316. Thereafter, for a patient who is not exhibiting expiratory airflow limitation, $P_L$ decreases gradually over exhalation to about the PEEP level (in this example, about 5 cmH$_2$O). For some patients, $P_L$ may be slightly greater than the PEEP setting due to a condition called "air trapping," which is also referred to as intrinsic PEEP (PEEP$_i$) or Auto-PEEP.

FIG. 3 further illustrates a method for deriving a delta P ($\Delta P$) time curve, which is illustrated in subsequent figures. Specifically, at the first moment of exhalation the ventilator calculates the difference between $P_L$ and $P_Y$ at the same value of time ($T_E$) as $T_E$ spans the interval between $T_E$=0 until $T_E$ exceeds about 300 ms (as shown, the dashed line represents $T_E''$ 318 at about 300 ms). In the example illustrated, $\Delta P''=P_L''$ 320−$P_Y''$ 322 at time $T_E''$ 318. Additionally, as illustrated, $Q_{NET}''$ 324 is the net flow at $T_E''$ 318.

Figure 4:
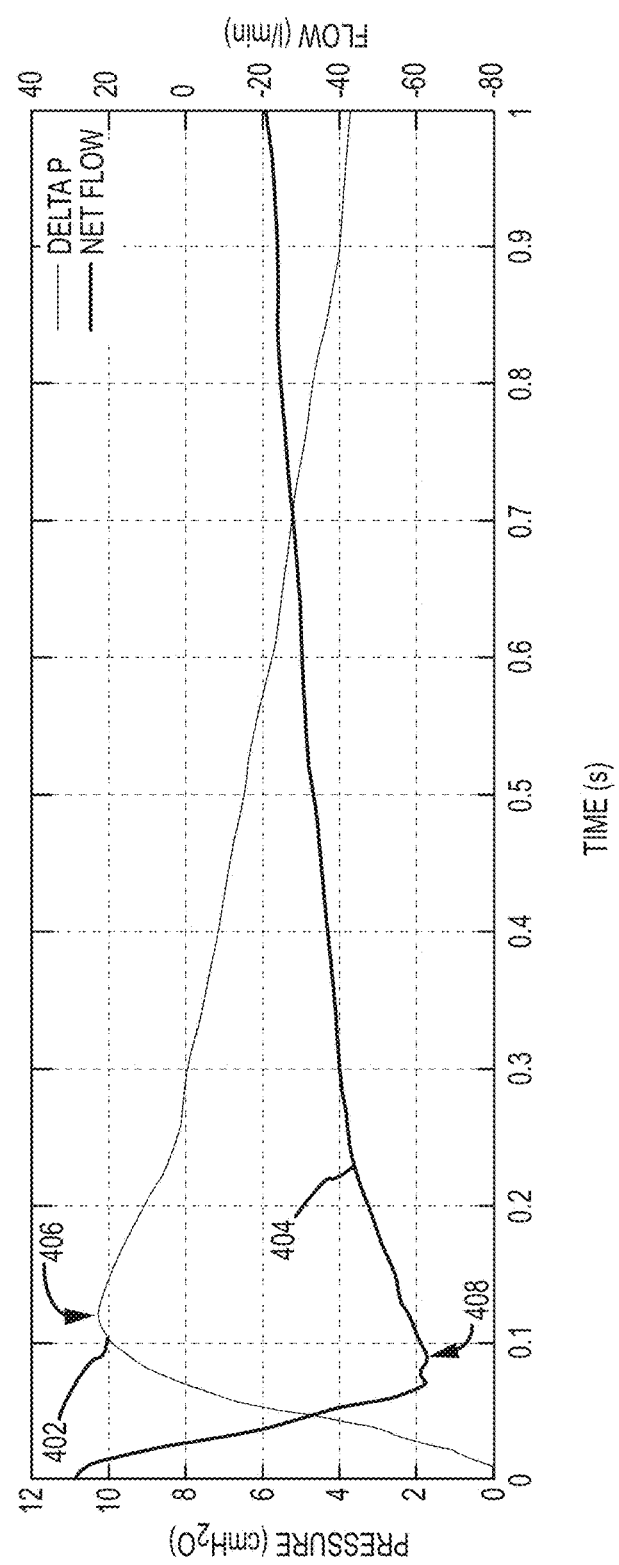
FIG. 4 is a graph illustrating pressure and flow waveforms during exhalation for an example patient who does not exhibit expiratory airflow limitation.

FIG. 4 is a graph illustrating pressure and flow waveforms during exhalation for an example patient who does not exhibit expiratory airflow limitation.

FIG. 4 provides a graphical representation of pressure and flow waveforms over time (in seconds) during an expiratory phase for a ventilated patient. Specifically, a delta pressure ($\Delta P$) waveform 402 is presented in units of centimeters of water (cmH$_2$O) and a net flow ($Q_{NET}$) waveform 404 is presented in units of liters per minute (l/min).

As described above, $\Delta P$ is the difference between the $P_Y$ waveform and the $P_L$ waveform. With reference to FIG. 3, $P_Y$ decreases sharply during about the first 100 ms of exhalation when the ventilator discontinues positive pressure and the direction of gas flow switches from entering to exiting the patient's lungs. Thereafter, for a patient who does not exhibit expiratory airflow limitation, $P_Y$ stabilizes and, as exhalation progresses, $P_Y$ declines gradually toward the clinician-set PEEP level (in this example, about 5 cmH$_2$O). $P_L$ also decreases gradually over exhalation to about the PEEP level (in this example, about 5 cmH$_2$O). Accordingly, for a patient who is not exhibiting expiratory airflow limitation, the difference between $P_L$ and $P_Y$ (or $\Delta P$) is greatest 406 shortly after about 100 ms of exhalation and gradually decreases as $P_L$ and $P_Y$ converge toward the PEEP setting at the end of exhalation. In embodiments, as $P_L$ may be greater than PEEP (which is the $P_Y$ target) at the end of exhalation, $\Delta P$ may be positive at the end of exhalation.

As illustrated by net flow ($Q_{NET}$) waveform 404, $Q_{NET}$ initially increases to a peak flow of about −60 l/min when gas flow switches from entering to exiting the lungs. After about the first 100 ms of exhalation, for a patient who does not exhibit expiratory airflow limitation, $Q_{NET}$ gradually decreases from about −60 l/min toward zero l/min at the end of exhalation, at which point equilibrium is reached and air no longer exits the lungs. In the example shown, exhalation may not be complete after 1 second and gases may continue to exit the lungs until $Q_{NET}$ is roughly equal to zero l/min (not shown).

Figure 5:
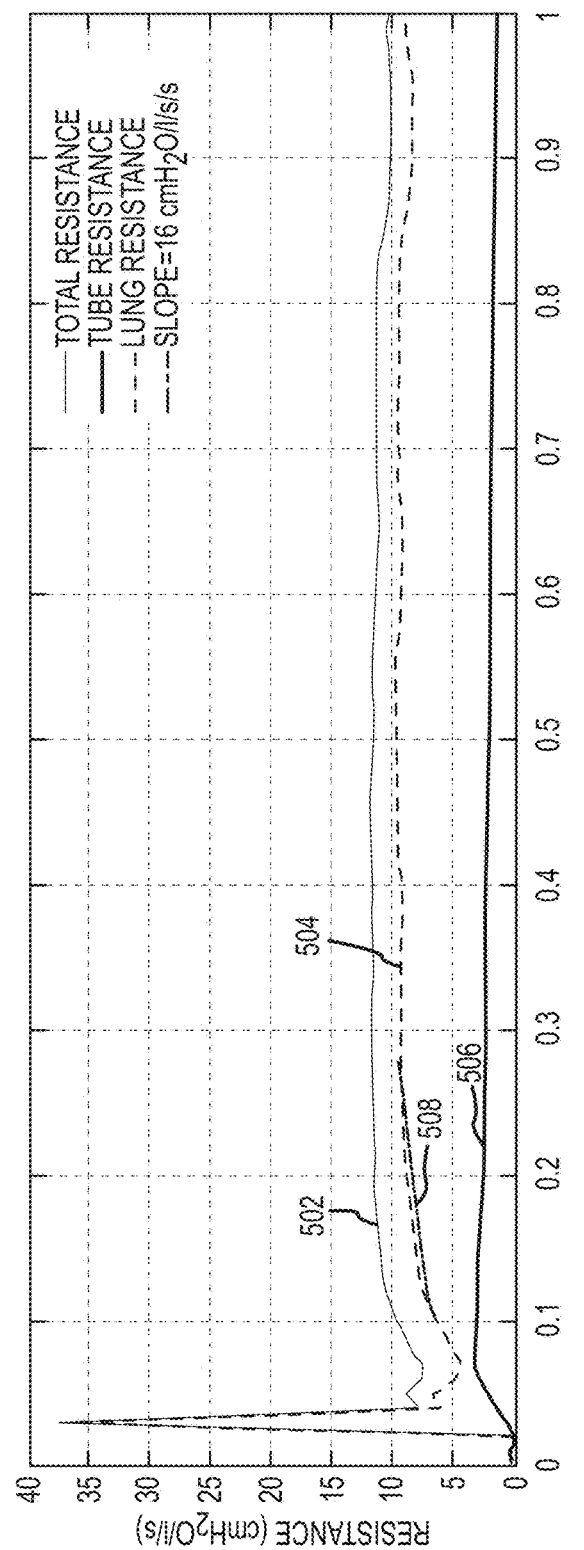
FIG. 5 is a graph illustrating expiratory resistance waveforms for an example patient who does not exhibit expiratory airflow limitation.

FIG. 5 is a graph illustrating resistance waveforms during exhalation for an example patient who does not exhibit expiratory airflow limitation.

FIG. 5 provides a graphical representation of resistance waveforms over time (in seconds) during an expiratory phase for a ventilated patient. Specifically, a total resistance ($R_{TOT}$) waveform 502 is presented in units of centimeters of water per liters per second (cmH$_2$O/l/s), a lung resistance ($R_L$) waveform 504 is presented in units of cmH$_2$O/l/s, and a tube resistance ($R_T$) waveform 506 is presented in units of cmH$_2$O/l/s.

In embodiments, during about the first 100 to 300 ms of exhalation, the $\Delta P$ waveform and the net flow ($Q_{NET}$) waveform may be evaluated to determine total resistance, $R_{TOT}$, based on the following equation: $R_{TOT}=\Delta P/Q_{NET}$. As described above, $R_{TOT}$ is equal to $R_L$ plus $R_T$. Accordingly, $R_L$ is equal to ($\Delta P$ divided by $Q_{NET}$) minus $R_T$ ($R_L=[\Delta P/Q_{NET}]-R_T$). As described above, $R_{TOT}$, $R_L$ and/or $R_T$ may be trended over time.

In embodiments, for a patient who does not exhibit expiratory airflow limitation, $R_L$ may increase gradually over the period between about 100 and 300 ms of exhalation. That is, the rate of change (or slope 508) of $R_L$ may increase at a relatively low rate between about 100 and 300 ms of exhalation (e.g., less than 100 cmH$_2$O/l/s/s). In the example shown, the slope 508 of the $R_L$ waveform 504 is equal to about 16 cmH$_2$O/l/s/s. In further embodiments, for a patient who does not exhibit expiratory airflow limitation, after about 300 ms of exhalation, the $R_L$ waveform may be relatively flat (or exhibit a slight decrease) for the remainder of exhalation.

Figure 6:
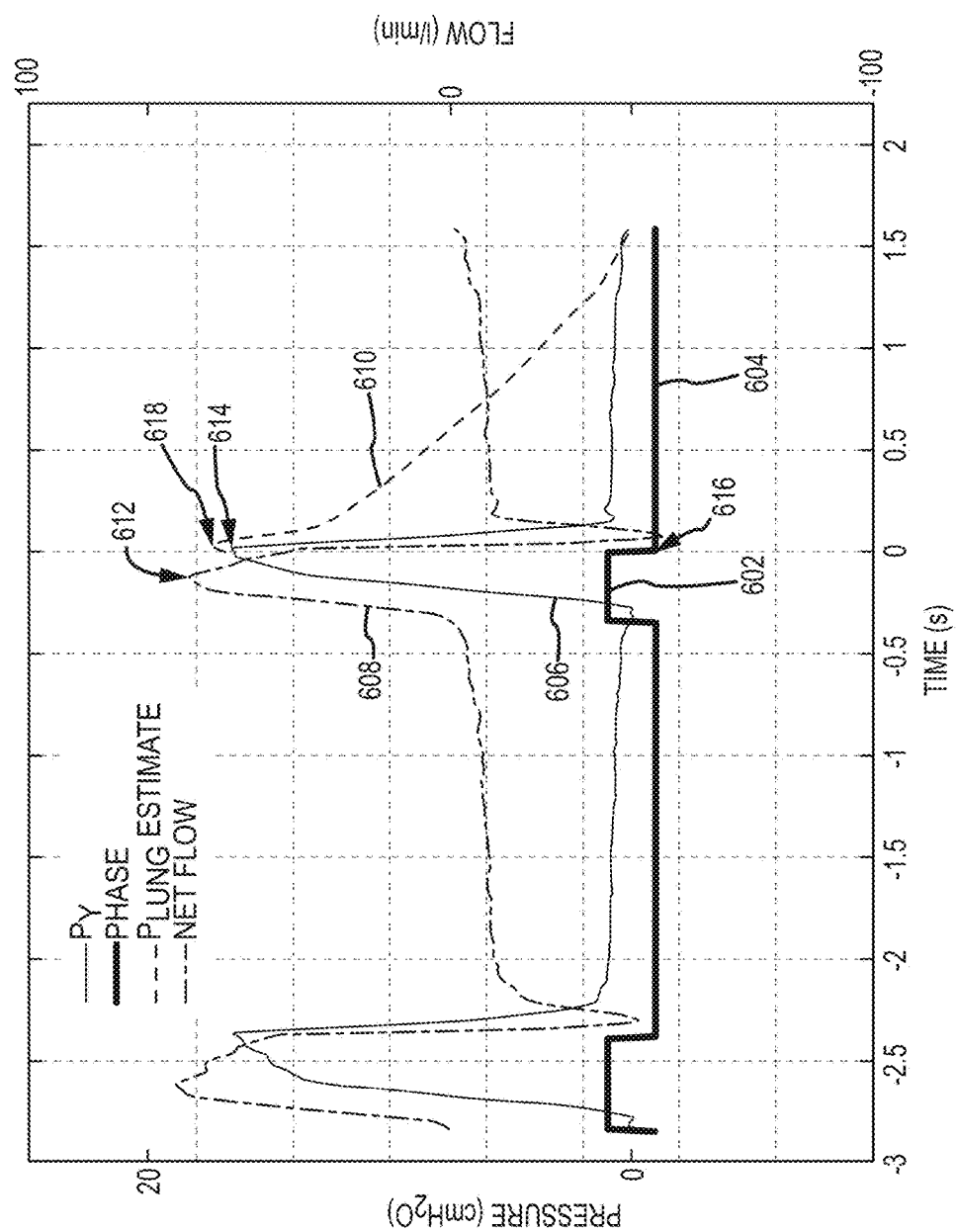
FIG. 6 is a graph illustrating pressure and flow waveforms for an example patient who exhibits expiratory airflow limitation.

FIG. 6 is a graph illustrating pressure and flow waveforms for an example patient who exhibits expiratory airflow limitation.

FIG. 6 provides a graphical representation of pressure and flow waveforms over time (in seconds) during an inspiratory phase 602 and an expiratory phase 604 of a breath cycle for a ventilated patient. A pressure ($P_Y$) measured during inspiration 602 is an inflation pressure ($P_{APPL}$) if it exceeds the initial end-exhalation pressure of the previous breath. That is, the pressure ($P_Y$) waveform 606 during inspiratory phase 602 is equivalent to $P_{APPL}$ as defined in this application. The inspiratory-expiratory pressure ($P_Y$) waveform 606 is presented in units of centimeters of water (cmH$_2$O), a net flow ($Q_{NET}$) waveform 608 is presented in units of liters per minute (l/min), and an estimated lung pressure ($P_L$) waveform 610 is presented in units of cmH$_2$O.

As illustrated by net flow $Q_{NET}$ waveform 608, inspiratory $Q_{NET}$ increases to a peak flow 612 around a middle part of inspiration and then decreases for the remainder of inspiration. Conceptually, the ventilator terminates inspiratory flow ($Q_{NET}$) at event 616. Thereafter, the ventilator enters the expiratory phase in which $Q_{NET}$ is assigned negative values by convention. Immediately after the beginning of exhalation 616, $Q_{NET}$ increases sharply to about −60 l/min as the direction of the flow of air switches from entering the lungs to exiting the lungs. Thereafter, $Q_{NET}$ decreases sharply within about the first 100-200 ms of exhalation to about −50 l/min. Thereafter, as exhalation progresses, $Q_{NET}$ gradually decreases toward zero l/min at the end of exhalation, at which point equilibrium is reached and expired volume no longer exits the lungs. In cases of severe expiratory airflow limitation, flow may not reach zero at the end of exhalation, resulting in autoPEEP (or PEEP$_i$). As illustrated by FIG. 6, when equilibrium is reached before $Q_{NET}$ reaches zero at the end of exhalation, the example patient is maintained in a state of perpetual autoPEEP. As should be appreciated, with reference to FIG. 3, for a patient not exhibiting expiratory airflow limitation, $Q_{NET}$ decreases at a relatively steady rate from about 100 ms to the end of exhalation. In contrast, for a patient exhibiting expiratory airflow limitation, $Q_{NET}$ decreases sharply in the first 100-200 ms of exhalation, and then decreases gradually at a relatively slower, steady rate to the end of exhalation with a high likelihood that the following inspiration will begin before exhalation is complete.

As illustrated by pressure ($P_Y$) waveform 606, $P_{APPL}$ increases to a peak pressure 614 at the end of inspiration. At the beginning of exhalation 616, $P_Y$ ($P_{APPL}$ technically transitions to $P_Y$ at 616) decreases sharply in the first 100-200 ms of exhalation when the ventilator discontinues positive pressure to the patient airway and recoil force of the combined lungs and thorax drives gas out of the patient's lungs. In fact, in the case of a patient exhibiting severe expiratory airflow limitation, $P_Y$ may decline almost to the clinician-set PEEP level within the first 100-200 ms of exhalation. Thereafter, $P_Y$ may abruptly stabilize and, as exhalation progresses, gradually decrease at a minimal rate toward the clinician-set PEEP level. In some cases (not illustrated here), with PEEP set to finite positive values, the PEEP controller may for a brief interval in early exhalation automatically set the PEEP target to near atmospheric, atmospheric, or below atmospheric pressure to enhance the pressure gradient driving gas from the lungs. As should be appreciated, with reference to FIG. 3, for a patient not exhibiting expiratory airflow limitation, $P_Y$ decreases at a relatively steady rate after the first 100 ms of exhalation toward the clinician-set PEEP level. In contrast, for a patient exhibiting expiratory airflow limitation, $P_Y$ decreases sharply to almost the clinician-set PEEP level in the first 100-200 ms of exhalation, and then decreases gradually at a minimal rate to the end of exhalation. That is, in either case, the $P_Y$ curve is somewhat biconcave during exhalation. However, in the case of expiratory airflow limitation, the biconcave appearance is enhanced. Moreover, in the case of expiratory airflow limitation, the flow curve is exaggerated.

As illustrated by $P_L$ waveform 610, at the beginning of exhalation 616, $P_L$ increases to peak $P_L$ 618, which is greater than peak $P_{APPL}$ 614. Thereafter, for a patient who exhibits expiratory airflow limitation, $P_L$ decreases sharply in the first 100-200 ms of exhalation and then decreases gradually over the remainder of exhalation to about the clinician-set PEEP level (in this case, about 0 cmH$_2$O). In this example, the P$_L$ and the P$_Y$ waveforms converge at atmospheric pressure (about 0 cmH$_2$O) at the end of exhalation.

Although not illustrated on FIG. 6, the method for deriving the delta P (ΔP) curve discussed in connection with FIG. 3 applies to FIG. 6. At the first moment of exhalation the ventilator calculates the difference between P$_L$ and P$_Y$ at corresponding values of T$_E$ until T$_E$ exceeds about 300 ms.

Figure 7:
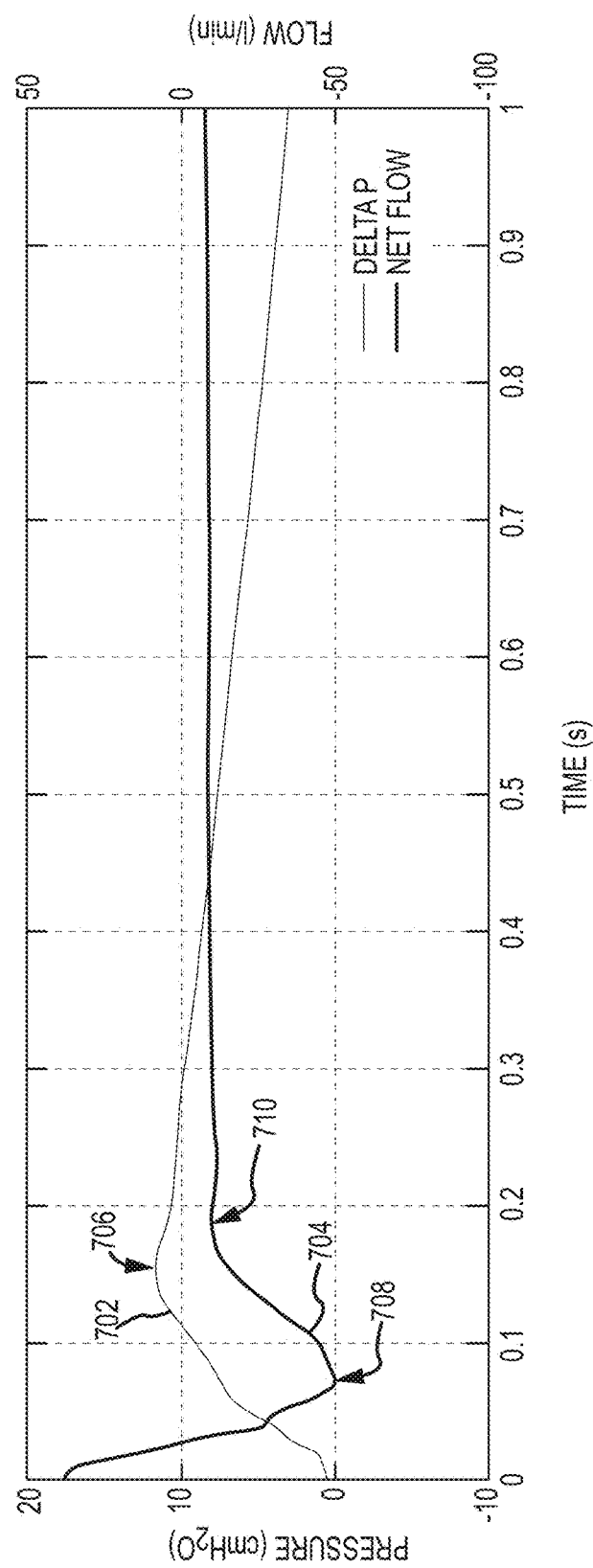
FIG. 7 is a graph illustrating pressure and flow waveforms during exhalation for an example patient who exhibits expiratory airflow limitation.

FIG. 7 is a graph illustrating pressure and flow waveforms during exhalation for an example patient who exhibits expiratory airflow limitation.

FIG. 7 provides a graphical representation of pressure and flow waveforms over time (in seconds) during an expiratory phase for a ventilated patient. Specifically, a delta pressure (ΔP) waveform 702 is presented in units of centimeters of water (cmH$_2$O) and a net flow (Q$_{NET}$) waveform 704 is presented in units of liters per minute (l/min).

As described above, ΔP is the difference between the P$_Y$ waveform and the P$_L$ waveform. With reference to FIG. 6, for a patient who exhibits expiratory airflow limitation, P$_Y$ decreases sharply to almost the clinician-set PEEP level during about the first 100-200 ms of exhalation. Thereafter, P$_Y$ stabilizes, declining at a noticeably lower rate toward the clinician-set PEEP level as exhalation progresses (in this example, PEEP is set to zero). In contrast, P$_L$ increases to peak P$_L$ and then decreases sharply in the first 100-200 ms of exhalation. Thereafter, P$_L$ decreases gradually over the remainder of exhalation to about the clinician-set PEEP level. Accordingly, for a patient who is exhibiting expiratory airflow limitation, the difference between P$_L$ and P$_Y$ (or ΔP) is greatest 706 shortly after about 100 ms of exhalation and gradually decreases as P$_L$ and P$_Y$ converge toward the PEEP setting at the end of exhalation.

As illustrated by Q$_{NET}$ waveform 704, for a patient who exhibits expiratory airflow limitation, Q$_{NET}$ increases to a peak expiratory flow of about −50 l/min (point 708) just after beginning exhalation when gas flow switches from entering to exiting the lungs. Between about 100 and 200 ms of exhalation, Q$_{NET}$ decreases sharply from about −50 l/min (point 708) to about −10 l/min (point 710). After approximately 200 ms of exhalation, Q$_{NET}$ appears to linearly decrease toward about zero l/min, indicating air can no longer exit the lungs. For the example patient shown, exhalation may not be complete after 1 second and gases may continue to exit the lungs until Q$_{NET}$ is approximately equal to zero l/min (not shown).

Figure 8:
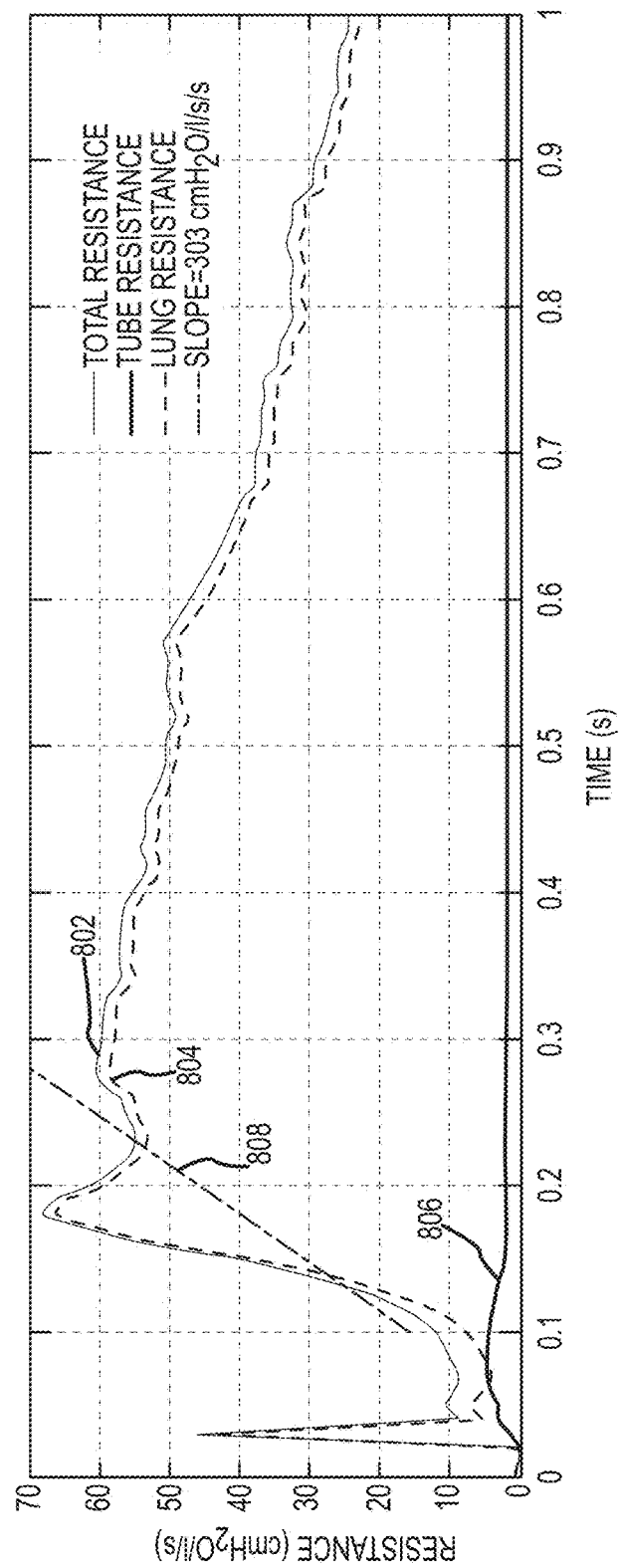
FIG. 8 is a graph illustrating expiratory resistance waveforms for an example patient who exhibits expiratory airflow limitation.

FIG. 8 is a graph illustrating resistance waveforms during exhalation for an example patient who exhibits expiratory airflow limitation.

FIG. 8 provides a graphical representation of resistance waveforms over time (in seconds) during an expiratory phase for a ventilated patient. Specifically, a total resistance (R$_{TOT}$) waveform 802 is presented in units of centimeters of water per liter per second (cmH$_2$O/l/s), a lung resistance (R$_L$) waveform 804 is presented in units of cmH$_2$O/l/s, and a tube resistance (R$_T$) waveform 806 is presented in units of cmH$_2$O/l/s.

In embodiments, during about the first 100 to 300 ms of exhalation, the ΔP waveform and the net flow (Q$_{NET}$) waveform may be evaluated to determine total resistance, R$_{TOT}$, based on the following equation: R$_{TOT}$=ΔP/Q$_{NET}$. As described above, R$_{TOT}$ is equal to R$_L$ plus R$_T$. Accordingly, R$_L$ is equal to (ΔP divided by Q$_{NET}$) minus R$_T$ (R$_L$=[ΔP/Q$_{NET}$]−R$_T$). Moreover, as described above, R$_{TOT}$, R$_L$ and/or R$_T$ may be trended over time.

In embodiments, for a patient who exhibits expiratory airflow limitation, R$_L$ (or R$_{TOT}$) may increase sharply over the period between about 100 and 300 ms of exhalation. That is, the rate of change (or slope 808) of R$_L$ may increase quickly between about 100 and 300 ms of exhalation (e.g., a slope of more than approximately 100 cmH$_2$O/l/s/s). For a patient who exhibits expiratory airflow limitation, this sharp increase in resistance occurs because the bronchioles constrict shortly after the start of exhalation (greatly increasing expiratory resistance due to anatomical structures, R$_L$). This increase in expiratory resistance further causes a sharp decrease in the airflow exiting the lungs between about 100 and 200 ms of exhalation (see FIG. 7, Q$_{NET}$ waveform 704).

In the example shown, the slope 808 of the R$_L$ waveform 804 is equal to approximately 303 cmH$_2$O/l/s/s. In further embodiments, for a patient who exhibits expiratory airflow limitation, after about 300 ms of exhalation, the R$_L$ waveform decreases gradually for the remainder of exhalation. In contrast, with reference to FIG. 5, for a patient who does not exhibit expiratory airflow limitation, the slope of expiratory resistance lies below a defined threshold value (slope_R$_L$ threshold) and, after approximately 300 ms of exhalation, the slope of the R$_L$ waveform is approximately constant until ΔP and Q$_{NET}$ lose resolution.

Figure 9:
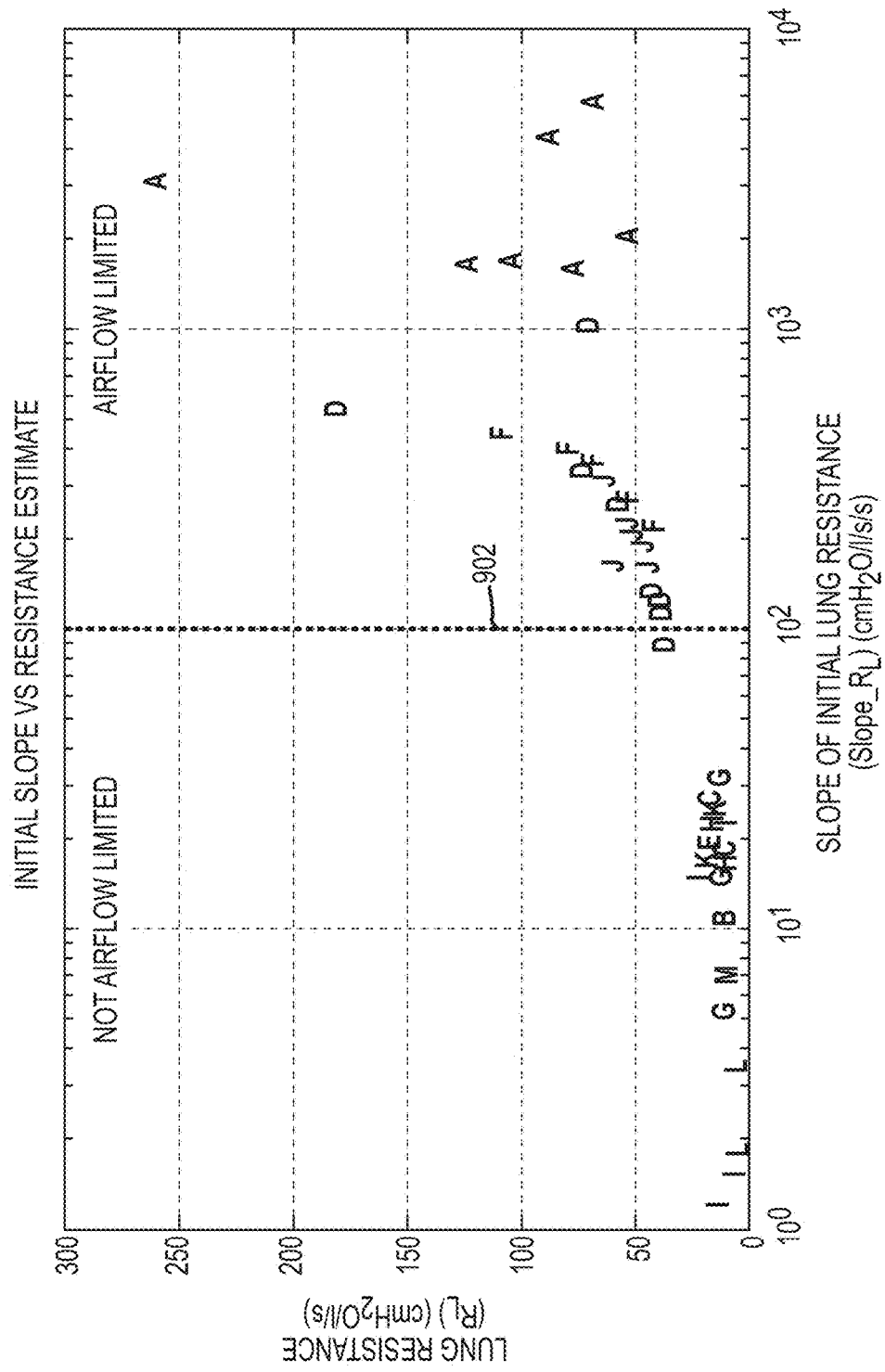
FIG. 9 is a graph illustrating the slope of initial expiratory lung resistance versus expiratory lung resistance values for a group of ventilated patients.

FIG. 9 is a graph illustrating the slope of resistance versus resistance values for a group of ventilated patients.

FIG. 9 provides a comparison of patients who exhibit expiratory airflow limitation and patients who do not exhibit expiratory airflow limitation. Specifically, FIG. 9 displays lung resistance (R$_L$) in units of cmH$_2$O/l/s versus the slope of R$_L$ (slope_R$_L$) in units of cmH$_2$O/l/s/s for the group of ventilated patients. The group of ventilated patients is described in Table 1 below.

TABLE 1

| Patient | Symptoms and/or Diagnosis | Expiratory Airflow Limitation? |
|---|---|---|
| A | COPD | Expiratory Airflow Limitation |
| B | Acute Respiratory Failure (ARF) with COPD | |
| C | ARF | |
| D | COPD | Expiratory Airflow Limitation |
| E | ARF | |
| F | COPD | Expiratory Airflow Limitation |
| G | ARF with Pulmonary Edema and COPD | |
| H | ARF | |
| I | ARF with Pulmonary Edema, moderate COPD, obesity | |
| J | COPD | Expiratory Airflow Limitation |
| K | ARF | |
| L | ARF with COPD | |
| M | Coma | |

As provided in Table 1, while patients A, B, D, F, G, I, J, and L have been diagnosed with COPD, only patients A, D, F, and J exhibit COPD with expiratory airflow limitation. Accordingly, a method for distinguishing between COPD patients who exhibit and who do not exhibit expiratory airflow limitation would be advantageous.

FIG. 9 illustrates R$_L$ data for one or more breaths for each of patients A-M. A slope_R$_L$ threshold 902 of 100 cmH$_2$O/l/s/s is identified by a dashed line. As illustrated by FIG. 9, the slope_R$_L$ data for patients B, C, E, G, H, I, K, L, and M fall below the slope_R$_L$ threshold 902. According to embodiments, by comparing the slope_R$_L$ data to the slope_R$_L$ threshold 902, it may be determined that patients B, C, E, G, H, I, K, L, and M do not exhibit expiratory airflow limitation. Indeed, as provided in Table 1, patients B, C, E, G, H, I, K, L, and M do not exhibit expiratory airflow limitation.

As illustrated by FIG. 9, the slope_$R_L$ data for patients A, F and J fall above the slope_$R_L$ threshold 902 for each of a plurality of breaths. According to embodiments, by comparing the slope_$R_L$ data to the slope_$R_L$ threshold 902, it may be determined that patients A, F and J exhibit expiratory airflow limitation. Indeed, as provided in Table 1, patients A, F and J exhibit expiratory airflow limitation.

With respect to patient D, the slope_$R_L$ data for one breath falls below the slope_$R_L$ threshold 902, and the slope_$R_L$ data for seven breaths fall above the slope_$R_L$ threshold 902. That is, for patient D, in 7 of 8 breaths, the slope_$R_L$ data fall above the slope_$R_L$ threshold 902. According to embodiments, by comparing the slope_$R_L$ data to the slope_$R_L$ threshold 902 over a threshold number of breaths (e.g., 6 of 8) or a threshold percentage of breaths (e.g., 75%), it may be determined that patient D exhibits expiratory airflow limitation. Indeed, as provided in Table 1, patient D exhibits expiratory airflow limitation.

Figure 10:
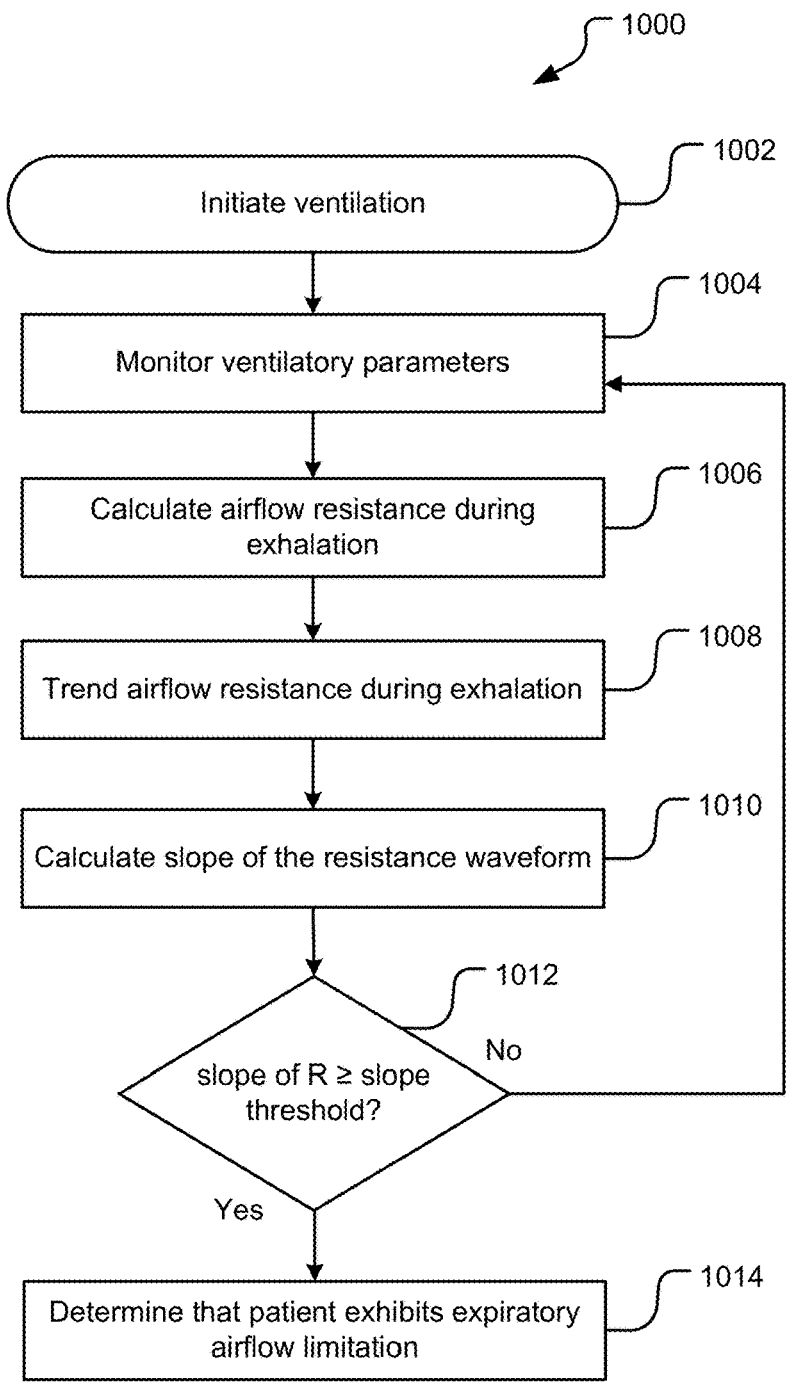
FIG. 10 is a flow chart illustrating an embodiment of a method for determining whether a ventilated patient exhibits expiratory airflow limitation.

FIG. 10 is a flow chart illustrating an embodiment of a method for determining whether a ventilated patient exhibits expiratory airflow limitation.

Method 1000 begins with an initiate ventilation operation 1002. Initiate ventilation operation 1002 may further include various additional operations. For example, initiate ventilation operation 1002 may include receiving one or more ventilatory settings associated with ventilation of a patient, e.g., a clinician-selected PEEP level, an inspiratory pressure ($P_I$), a tidal volume ($V_T$), a clinician-selected amount of support pressure, etc. Upon receiving the one or more ventilatory settings, the ventilator may initiate ventilation based on a selected breath type, e.g., a pressure-targeted, volume-targeted, mandatory, or spontaneous breath type.

At monitor operation 1004, the ventilator may monitor various ventilatory parameters, including volume, pressure, flow, etc. For example, the ventilator may monitor ventilator-applied inflation pressure ($P_{APPL}$) by any suitable means, e.g., via one or more pressure transducers associated with the patient circuit, patient wye, or any ventilator component or module (e.g., a face mask). Moreover, in embodiments, the ventilator may calculate or otherwise estimate lung pressure ($P_L$). For example, where other variables are known, $P_L$ may be calculated based on the Equation of Motion ($P_{MUS}+P_{APPL}=V_T/C+R*Q$), as described above. The ventilator may further trend pressure ($P_{APPL}$ or $P_Y$, as appropriate) over time to provide a pressure ($P_Y$) waveform and may trend $P_L$ over time to provide a $P_L$ waveform. In embodiments, the pressure ($P_Y$) waveform and/or the $P_L$ waveform may be trended over one or more inspiratory and expiratory phases for the ventilated patient. Additionally, the ventilator may calculate $\Delta P$, which is the difference between $P_Y$ and $P_L$. In embodiments, the ventilator may also trend $\Delta P$ over time to provide a $\Delta P$ waveform.

In further embodiments, at monitor operation 1004, the ventilator may monitor flow (Q) by any suitable means, e.g., via one or more flow sensors associated with the patient circuit, patient wye, or any ventilator component or module. In some embodiments, the flow signal received from the flow sensors may be compensated for humidity, or other consideration, to provide net flow, $Q_{NET}$. As with other ventilatory parameters, $Q_{NET}$ may be trended over time to provide a $Q_{NET}$ waveform over one or more inspiratory and expiratory phases for the ventilated patient.

At calculate operation 1006, the ventilator may calculate resistance for the ventilated patient. For example, the $\Delta P$ waveform and the $Q_{NET}$ waveform may be evaluated to determine total resistance, $R_{TOT}$, based on the following equation: $R_{TOT}=\Delta P/Q_{NET}$. As described above, $R_{TOT}$ is equal to lung resistance ($R_L$) plus tube resistance ($R_T$). Accordingly, $R_L$ is equal to ($\Delta P$ divided by $Q_{NET}$) minus $R_T$ ($R_L=[\Delta P/Q_{NET}]-R_T$). Since $R_T$ a function of gas flow, knowing the tube type and size allows its value to be obtained using a lookup table or other standardized formula.

At trend operation 1008, the ventilator may trend $R_{TOT}$, $R_L$ and/or $R_T$ over time to provide $R_{TOT}$, $R_L$ and/or $R_T$ waveforms. In embodiments, the ventilator may trend $R_{TOT}$, $R_L$ and/or $R_T$ over time during one or more expiratory phases for a ventilated patient.

At calculate slope operation 1010, the ventilator may calculate a slope of the resistance waveform for the ventilated patient. In embodiments, the ventilator may calculate the slope of the resistance waveform between the first 100 and 300 ms of exhalation for a ventilated patient. In some embodiments, the ventilator may calculate the slope of the $R_L$ waveform between the first 100 and 300 ms of exhalation for a ventilated patient.

At determination operation 1012, the ventilator may compare the slope of the resistance waveform with a defined slope of resistance threshold. In some embodiments, the ventilator may compare the slope of the $R_L$ waveform with a defined slope of lung resistance threshold (slope_$R_L$ threshold). In other embodiments, the ventilator may compare the slope of the $R_{TOT}$ waveform with a defined slope of total resistance threshold (slope_$R_{TOT}$ threshold). The slope $R_L$ threshold and the slope_$R_{TOT}$ threshold may be determined by any suitable means. For example, the slope_$R_L$ and slope_$R_{TOT}$ thresholds may be determined by statistically analyzing resistance data for a group of ventilated patients, some of which exhibit expiratory airflow limitation and some of which do not exhibit expiratory airflow limitation. In some embodiments, the slope_$R_L$ threshold may be equal to approximately 100 cmH$_2$O/l/s/s. If the slope of the $R_L$ waveform is greater than or equal to the slope_$R_L$ threshold, or the slope of the $R_{TOT}$ waveform is greater than or equal to the slope_$R_{TOT}$ threshold, the ventilator may progress to determine operation 1014. Alternatively, if the slope of the $R_L$ waveform is less than the slope_$R_L$ threshold, or the slope of the $R_{TOT}$ waveform is less than the slope_$R_{TOT}$ threshold, the ventilator may return to monitor operation 1004.

At determine operation 1014, where the slope of the $R_L$ waveform is greater than or equal to the slope_$R_L$ threshold, or the slope of the $R_{TOT}$ waveform is greater than or equal to the slope_$R_{TOT}$ threshold, the ventilator may determine that the ventilated patient exhibits expiratory airflow limitation. According to embodiments, when the patient exhibits expiratory airflow limitation during exhalation, the ventilator may recommend or automatically adjust the ventilatory settings to provide sufficient ventilation to the patient. For example, appropriate changes may include, but are not limited to, an adjusted WOB estimation (e.g., using a default value for R) for the proportional assist ventilation breath type, a lower respiratory rate (resulting in a higher expiratory time ($T_E$) for complete exhalation of gases), an alternate waveform setting for mandatory breath types, etc.

As should be appreciated, the particular steps of method 1000 described above are not exclusive and, as will be understood by those skilled in the art, the particular ordering of steps as described herein is not intended to limit the method, e.g., steps may be performed in differing order, additional steps may be performed, and disclosed steps may be excluded without departing from the spirit of the present disclosure.

Figure 11:
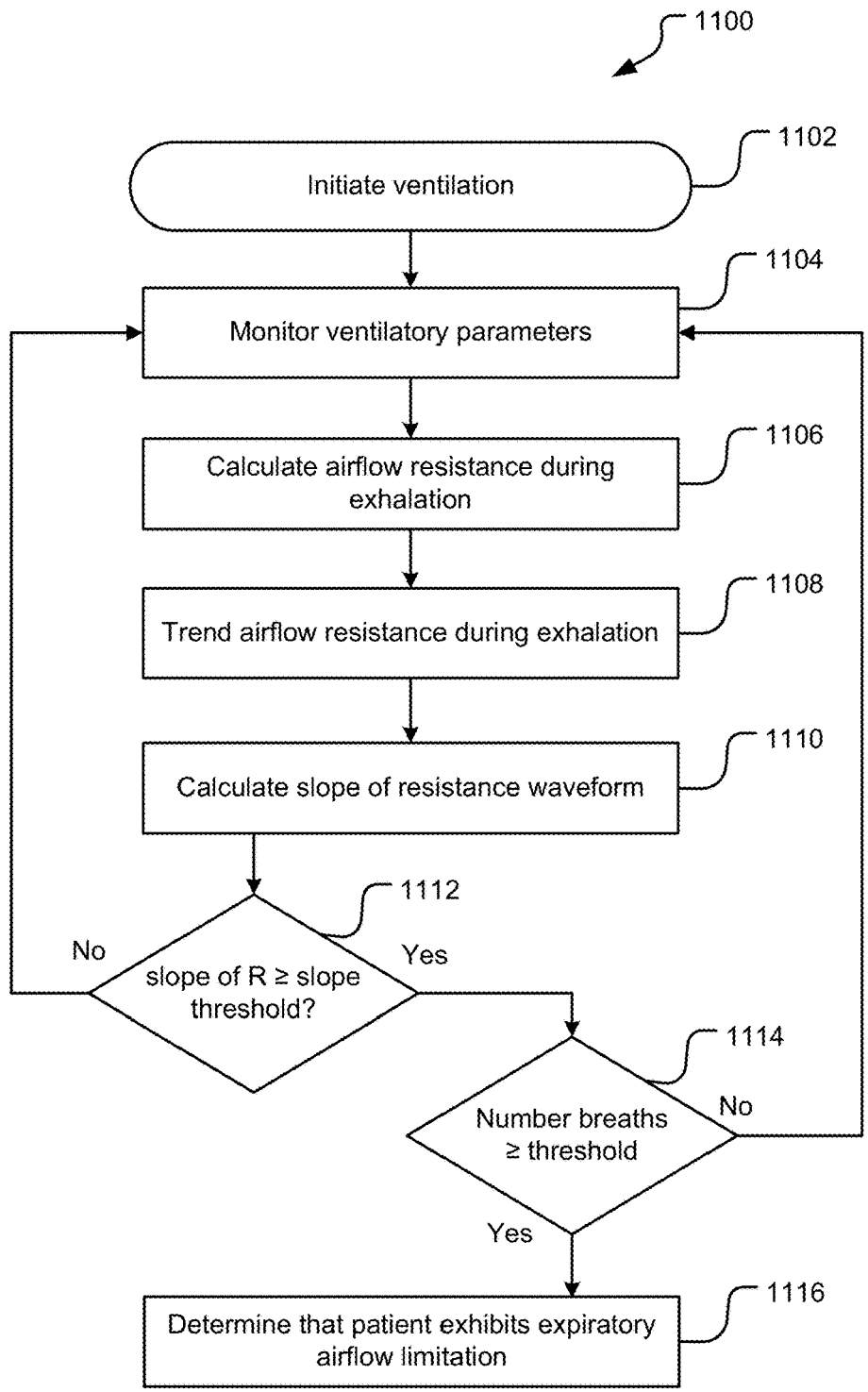
FIG. 11 is a flow chart illustrating another embodiment of a method for determining whether a ventilated patient exhibits expiratory airflow limitation.

FIG. 11 is a flow chart illustrating another embodiment of a method for determining whether a ventilated patient exhibits expiratory airflow limitation.

Method 1100 begins with an initiate ventilation operation 1102. Initiate ventilation operation 1102 is similar to initiate ventilation operation 1002, as described above.

At monitor operation 1104, the ventilator may monitor various ventilatory parameters, including volume, pressure, flow, etc., as described with respect to monitor operation 1004. For example, the ventilator may monitor and trend pressure ($P_{APPL}$ or $P_Y$, as appropriate) and may estimate and trend lung pressure ($P_L$) by any suitable means. Additionally, at monitor operation 1104, the ventilator may calculate and trend $\Delta P$, which is the difference between $P_Y$ and $P_L$. In further embodiments, the ventilator may monitor and trend flow (Q) or net flow ($Q_{NET}$) by any suitable means.

At calculate operation 1106, the ventilator may calculate resistance for the ventilated patient as described with respect to calculate operation 1006. For example, the $\Delta P$ waveform and the $Q_{NET}$ waveform may be evaluated to determine total resistance, $R_{TOT}$, based on the following equation: $R_{TOT} = \Delta P / Q_{NET}$. As described above, $R_{TOT}$ is equal to lung resistance ($R_L$) plus tube resistance ($R_T$). Accordingly, $R_L$ is equal to ($\Delta P$ divided by $Q_{NET}$) minus $R_T$ ($R_L = [\Delta P / Q_{NET}] - R_T$). Since $R_T$ a function of gas flow, knowing the tube type and size allows its value to be obtained using a lookup table or other standardized formula.

At trend operation 1108, the ventilator may trend $R_{TOT}$, $R_L$ and/or $R_T$ over time to provide $R_{TOT}$, $R_L$ and/or $R_T$ waveforms as described with respect to trend operation 1008. In embodiments, the ventilator may trend $R_{TOT}$, $R_L$ and/or $R_T$ over time during one or more expiratory phases for a ventilated patient.

At calculate slope operation 1110, the ventilator may calculate a slope of the resistance waveform for the ventilated patient as described with respect to calculate slope operation 1010. In embodiments, the ventilator may calculate the slope of the $R_L$ waveform between the first 100 and 300 ms of exhalation for a ventilated patient. In some embodiments, the ventilator may calculate the slope of the $R_{TOT}$ waveform between the first 100 and 300 ms of exhalation for a ventilated patient.

At determination operation 1112, the ventilator may compare the slope of the $R_L$ waveform with a slope_$R_L$ threshold or the slope of the $R_{TOT}$ waveform with a slope_$R_{TOT}$ threshold, as described with respect to determination operation 1012. The slope_$R_L$ threshold and the slope_$R_{TOT}$ threshold may be determined by any suitable means. In some embodiments, the slope_$R_L$ threshold may be equal to approximately 100 cmH$_2$O/l/s/s. If the slope of the $R_L$ waveform is greater than or equal to the slope_$R_L$ threshold, or the slope of the $R_{TOT}$ waveform is greater than or equal to the slope_$R_{TOT}$ threshold, the ventilator may progress to determination operation 1114. Alternatively, if the slope of the $R_L$ waveform is less than the slope_$R_L$ threshold, or the slope of the $R_{TOT}$ waveform is less than the slope_$R_{TOT}$ threshold, the ventilator may return to monitor operation 1104.

At determination operation 1114, the ventilator may compare the number of breaths in which the slope of the $R_L$ waveform breaches the slope_$R_L$ threshold or the $R_{TOT}$ waveform breaches the slope_$R_{TOT}$ threshold to a breath threshold (or a percentage threshold). For example, the breath threshold may require that, for a certain number of breaths, the slope of the $R_L$ waveform (or the $R_{TOT}$ waveform) is greater than or equal to the slope_$R_L$ threshold (or the slope_$R_{TOT}$ threshold, respectively), e.g., for 4 of 5 consecutive breaths, for 5 of 10 consecutive breaths, etc. In embodiments, the breath threshold may be determined by any suitable means, e.g., by statistically analyzing resistance data for a group of ventilated patients, some of which exhibit expiratory airflow limitation and some of which do not exhibit expiratory airflow limitation. In other embodiments, a percentage threshold may require that, for a certain percentage of breaths, the slope of the $R_L$ waveform (or the $R_{TOT}$ waveform) is greater than or equal to the slope_$R_L$ threshold (or the slope_$R_{TOT}$ threshold, respectively), e.g., for 60% of breaths, for 75% of breaths, etc. In embodiments, the percentage threshold may be determined by any suitable means, e.g., as described above for the breath threshold. If the number of breaths in which the slope of the $R_L$ waveform (or the $R_{TOT}$ waveform) breaches the slope_$R_L$ threshold (or the slope_$R_{TOT}$ threshold, respectively) is greater than or equal to the breath threshold (or the percentage threshold), the method progresses to determine operation 1116. Alternatively, if the number of breaths in which the slope of the $R_L$ waveform (or the $R_{TOT}$ waveform) breaches the slope_$R_L$ threshold (or the slope_$R_{TOT}$ threshold, respectively) is less than the breath threshold (or the percentage threshold), the ventilator may return to monitor operation 1104.

At determine operation 1116, where the slope of the $R_L$ waveform (or the $R_{TOT}$ waveform) breaches the slope_$R_L$ threshold (or the slope_$R_{TOT}$ threshold, respectively) for a threshold number (or percentage) of breaths, the ventilator may determine that the ventilated patient exhibits expiratory airflow limitation. According to embodiments, when the patient exhibits expiratory airflow limitation during exhalation, the ventilator may recommend or automatically adjust the ventilatory settings to provide sufficient ventilation to the patient. For example, appropriate changes may include, but are not limited to, an adjusted WOB estimation (e.g., using a default value for R) for the proportional assist ventilation breath type, a lower respiratory rate (resulting in a higher expiratory time ($T_E$) for complete exhalation of gases), an alternate waveform setting for mandatory breath types, etc.

As should be appreciated, the particular steps of method 1100 described above are not exclusive and, as will be understood by those skilled in the art, the particular ordering of steps as described herein is not intended to limit the method, e.g., steps may be performed in differing order, additional steps may be performed, and disclosed steps may be excluded without departing from the spirit of the present disclosure.

It will be clear that the systems and methods described herein are well adapted to attain the ends and advantages mentioned as well as those inherent therein. Those skilled in the art will recognize that the methods and systems within this specification may be implemented in many manners and as such is not to be limited by the foregoing exemplified embodiments and examples. In other words, functional elements being performed by a single or multiple components, in various combinations of hardware and software, and individual functions can be distributed among software applications at either the client or server level. In this regard, any number of the features of the different embodiments described herein may be combined into one single embodiment and alternative embodiments having fewer than or more than all of the features herein described are possible.

While various embodiments have been described for purposes of this disclosure, various changes and modifications may be made which are well within the scope of the present disclosure. Numerous other changes may be made which will readily suggest themselves to those skilled in the art and which are encompassed in the spirit of the disclosure and as defined in the appended claims.

What is claimed is:

1. A ventilator-implemented method for determining whether a ventilated patient exhibits an expiratory airflow limitation, the method comprising:
   delivering a flow of gases to a patient;
   monitoring ventilatory parameters;
   trending airflow resistance over time during an expiratory phase to produce a resistance waveform, wherein airflow resistance is a measure of frictional forces hampering the delivered flow of gases;
   calculating a slope of the resistance waveform for an initial portion of the expiratory phase;
   comparing the slope of the initial portion of the expiratory phase of the resistance waveform to a defined slope threshold;
   determining that the patient exhibits an expiratory airflow limitation when the slope of the initial portion of the expiratory phase of the resistance waveform is greater than or equal to the defined slope threshold; and
   in response to a determination that the patient exhibits the expiratory airflow limitation, adjusting at least one ventilatory setting.

2. The method of claim 1, further comprising:
   determining that the patient does not exhibit an expiratory airflow limitation when the slope of the initial portion of the expiratory phase of the resistance waveform is less than the defined slope threshold.

3. The method of claim 1, wherein the airflow resistance is lung resistance.

4. The method of claim 1, wherein the airflow resistance is total resistance.

5. The method of claim 1, further comprising:
   determining that the patient exhibits an expiratory airflow limitation when the slope of the resistance waveform is greater than or equal to the defined slope threshold for a threshold number of breaths.

6. The method of claim 1, further comprising:
   determining that the patient exhibits expiratory airflow limitation when the slope of the resistance waveform is greater than or equal to the defined slope threshold for a threshold percentage of breaths.

7. The method of claim 1, wherein the defined slope threshold is a lung resistance slope threshold (slope_$R_L$ threshold).

8. A system, comprising:
   at least one processor; and
   at least one memory, communicatively coupled to the at least one processor and containing instructions that, when executed by the at least one processor, cause a controller to determine whether a ventilated patient exhibits expiratory airflow limitation, the controller comprising:
      a gas source for delivering a flow of gases to a patient;
      a monitoring module for monitoring ventilatory parameters;
      an expiratory resistance detection module for:
         calculating airflow resistance during an expiratory phase;
         trending airflow resistance over time during the expiratory phase to produce a resistance waveform, wherein airflow resistance is a measure of frictional forces hampering the delivered flow of gases;
      an expiratory airflow limitation detection module for:
         calculating a slope of the resistance waveform for an initial portion of the expiratory phase;
         comparing the slope of the initial portion of the expiratory phase of the resistance waveform to a defined slope threshold; and
         determining that the patient exhibits an expiratory airflow limitation when the slope of the initial portion of the expiratory phase of the resistance waveform is greater than or equal to the defined slope threshold; and
      a ventilation module for:
         in response to the determination that the patient exhibits the expiratory airflow limitation, adjusting at least one ventilatory setting.

9. The system of claim 8, the expiratory airflow limitation detection module further configured for determining that the patient does not exhibit an expiratory airflow limitation when the slope of the initial portion of the expiratory phase of the resistance waveform is less than the defined slope threshold.

10. The system of claim 8, wherein the airflow resistance is lung resistance.

11. The system of claim 8, wherein the airflow resistance is total resistance.

12. The system of claim 8, the expiratory airflow limitation detection module further configured for determining that the patient exhibits an expiratory airflow limitation when the slope of the resistance waveform is greater than or equal to the defined slope threshold for a threshold number of breaths.

13. The system of claim 8, the expiratory airflow limitation detection module further configured for determining that the patient exhibits an expiratory airflow limitation when the slope of the resistance waveform is greater than or equal to the defined slope threshold for a threshold percentage of breaths.

14. The system of claim 8, wherein the defined slope threshold is a total resistance slope threshold (slope_$R_{TOT}$ threshold).

15. A computer storage device storing instructions that, when executed by a processor, cause a controller to determine whether a ventilated patient exhibits an expiratory airflow limitation comprising:
   delivering a flow of gases to a patient;
   monitoring ventilatory parameters;
   trending airflow resistance over time during an expiratory phase to produce a resistance waveform, wherein airflow resistance is a measure of frictional forces hampering the delivered flow of gases;
   calculating a slope of the resistance waveform for an initial portion of the expiratory phase;
   comparing the slope of the initial portion of the expiratory phase of the resistance waveform to a defined slope threshold;
   determining that the patient exhibits an expiratory airflow limitation when the slope of the initial portion of the expiratory phase of the resistance waveform is greater than or equal to the defined slope threshold;
   in response to the determination that the patient exhibits the expiratory airflow limitation, adjusting at least one ventilatory setting.

16. The computer storage device of claim 15, the controller further configured for determining that the patient does not exhibit an expiratory airflow limitation when the slope of the initial portion of the expiratory phase of the resistance waveform is less than the defined slope threshold.

17. The computer storage device of claim 15, wherein the airflow resistance is lung resistance.

18. The computer storage device of claim 15, wherein the airflow resistance is total resistance.

19. The computer storage device of claim 15, the controller further configured for determining that the patient exhibits an expiratory airflow limitation when the slope of the resistance waveform is greater than or equal to the defined slope threshold for a threshold number of breaths.

20. The computer storage device of claim 15, the controller further configured for determining that the patient exhibits an expiratory airflow limitation when the slope of the resistance waveform is greater than or equal to the defined slope threshold for a threshold percentage of breaths.

* * * * *